(12) United States Patent
Rabizadeh et al.

(10) Patent No.: US 12,072,337 B2
(45) Date of Patent: *Aug. 27, 2024

(54) CIRCULATING TUMOR CELL ENRICHMENT USING NEOEPITOPES

(71) Applicant: NANT HOLDINGS IP, LLC, Culver City, CA (US)

(72) Inventors: Shahrooz Rabizadeh, Culver City, CA (US); Kayvan Niazi, Culver City, CA (US); Nicholas J. Witchey, Culver City, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 662 days.

This patent is subject to a terminal disclaimer.

(21) Appl. No.: 16/615,360

(22) PCT Filed: May 21, 2018

(86) PCT No.: PCT/US2018/033683
§ 371 (c)(1),
(2) Date: Nov. 20, 2019

(87) PCT Pub. No.: WO2018/222433
PCT Pub. Date: Dec. 6, 2018

(65) Prior Publication Data
US 2020/0166515 A1    May 28, 2020

Related U.S. Application Data

(60) Provisional application No. 62/512,571, filed on May 30, 2017.

(51) Int. Cl.
*G01N 33/574* (2006.01)
*A61K 35/17* (2015.01)
*C07K 16/30* (2006.01)

(52) U.S. Cl.
CPC ....... *G01N 33/57492* (2013.01); *A61K 35/17* (2013.01); *C07K 16/30* (2013.01); *C07K 2317/21* (2013.01); *C07K 2317/24* (2013.01); *C07K 2317/565* (2013.01)

(58) Field of Classification Search
CPC ............ C07K 14/7051; C07K 2319/03; C07K 2317/622; C12N 5/0636; C12N 15/62; C12N 15/85; A61K 35/17
See application file for complete search history.

(56) References Cited

U.S. PATENT DOCUMENTS

| | | | |
|---|---|---|---|
| 2015/0252427 A1 | 9/2015 | Srivastava et al. | |
| 2016/0237163 A1 | 8/2016 | Sariel et al. | |

FOREIGN PATENT DOCUMENTS

| WO | 2012/159754 A2 | 11/2012 | |
|---|---|---|---|
| WO | 2014/180569 A1 | 11/2014 | |
| WO | WO-2015049688 A2 * | 4/2015 | ............ C07K 16/00 |
| WO | 2015/103037 A2 | 7/2015 | |
| WO | 2016/172722 A1 | 10/2016 | |
| WO | WO-2016172722 A1 * | 10/2016 | ............ A61K 35/17 |
| WO | 2017/066256 A2 | 4/2017 | |
| WO | 2017/066339 A1 | 4/2017 | |
| WO | WO-2017066339 A1 * | 4/2017 | ......... A61K 39/0011 |
| WO | 2017/194610 A1 | 11/2017 | |
| WO | 2018/222433 A2 | 12/2018 | |
| WO | 2018/222433 A3 | 12/2018 | |
| WO | 2018/222433 A4 | 12/2018 | |

OTHER PUBLICATIONS

US 8,569,009 B2, 10/2013, Lin et al. (withdrawn)
Rossi et al.M30 Neoepitope Expression in Epithelial Cancer: Quantification of Apoptosis in CirculatingTumor Cells by CellSearch Analysis.Clin Cancer Res; 16(21); 5233-43.2010. (Year: 2010).*
Rabia et al Understanding and overcoming trade-offs between antibody affinity,specificity, stability and solubility (Biochemical Engineering Journal 137 (2018) 365-374) (Year: 2018).*
Goel et al. Plasticity within the Antigen-Combining Site May Manifest as Molecular Mimicry in the Humoral Immune Response. J Immunol (2004) 173 (12): 7358-7367. (Year: 2004).*
Lloyd et al.Modelling the human immune response: performance of a 1011 human antibody repertoire against a broad panel of therapeutically relevant antigens. Protein Engineering, Design & Selection vol. 22 No. 3 pp. 159-168, 2009. (Year: 2009).*
Mohme et al Circulating and disseminated tumour cells—mechanisms of immune surveillance and escape. Nature Reviews Clinical Oncology, vol. 14, Mar. 2017, p. 155-p. 167 (Year: 2017).*
Pantel Functional Studies on Viable Circulating Tumor Cells (Clinical Chemistry 62:2 (328-334 (2016)) (Year: 2016).*
Yu Ex vivo culture of circulating breast tumor cells for individualized testing of drug susceptibility(Science, Jul. 11, 2014 • vol. 345 Issue 6193), (Year: 2014).*
Khoo Liquid biopsy and therapeutic response: Circulating tumor cell cultures for evaluation of anticancer treatment(Sci. Adv. 2016; 2 : e1600274 Jul. 13, 2016). (Year: 2016).*
Rossi et al.M30 Neoepitope Expression in Epithelial Cancer: Quantification of Apoptosis in Circulating Tumor Cells by CellSearch Analysis Clin Cancer Res; 16(21) Nov. 1, 2010, p. 5233-5243) (Year: 2010).*

(Continued)

*Primary Examiner* — Amy E Juedes
*Assistant Examiner* — Brian Hartnett
(74) *Attorney, Agent, or Firm* — Martin Fessenmaier; Umberg Zipser LLP

(57) ABSTRACT

Systems and methods for validating immune therapy that targets patient- and tumor-specific neoepitopes are presented in which cellular components are identified and/or used that present patient- and tumor-specific neoepitopes. Presence of these neoepitopes confirms the suitability of the neoepitopes. Advantageously, synthetic antibodies are created based on in silico analysis of the tumor genome and RNA or phage display, and can be used to isolate cellular components, and especially circulating tumor cells, metastatic cells, and/or exosomes and microvesicles.

13 Claims, 3 Drawing Sheets

(56) References Cited

OTHER PUBLICATIONS

Invitation pursuant to Rule 62a(1) EPC and Rule 63(1) EPC received for European Patent Application Serial No. 18808628.4 dated Feb. 11, 2021, 7 pages.
Brennick et al., "Neoepitopes as cancer immunotherapy targets: key challenges and opportunities", Immunotherapy, 2017, vol. 9, No. 4, pp. 361-371.
Newick et al., "Chimeric antigen receptor T-cell therapy for solid tumors", Oncolytics, 2016, vol. 3, No. 16006, pp. pp. 1-7.
Bordeaux et al., "Antibody validation", Biotechniques, 2010, vol. 48, No. 3, pp. 197-209.
Neuman et al., "Identification of target and cytotoxicity of novel monoclonal antibody NEO-201 in ovarian and uterine cancer subtypes", Gynecologic Oncology, 2016, vol. 141, pp. 95-96.
International Preliminary Report on Patentability Chapter II received for PCT Application Serial No. PCT/US2018/033683 dated Dec. 27, 2019, 14 pages.
European search report received for European Patent Application Serial No. 18808628.4 dated May 28, 2021, 10 pages.
International Search Report and Written Opinion received for PCT Application Serial No. PCT/US2018/033683 dated Jan. 21, 2019, 14 pages.
Kowalik et al., "Current approaches for avoiding the limitations of circulating tumor cells detection methods—implications for diagnosis and treatment of patients with solid tumors", Translation research, Jul. 2017, vol. 185, 42 pages.
Snyder et al., "Genetic Basis for Clinical Response to CTLA-4 Blockade in Melanoma", The New England Journal of Medicine, Dec. 4, 2014, vol. 371, No. 23, pp. 2189-2199.
European search report received for European Patent Application Serial No. 21192583.9 dated Dec. 2, 2021, 09 pages.
Communication pursuant to Article 94(3) EPC received for European Patent Application Serial No. 21192583.9 dated Dec. 21, 2023, 05 pages.
Xuebo et al., "Combinatorial libraries against libraries for selecting neoepitope activation-specific antibodies", Proceedings of the National Academy of Sciences, National Academy of Sciences, vol. 107, No. 14, Apr. 6, 2010 (Apr. 6, 2010), pp. 6252-6257.
Gros et al., "Prospective identification of neoantigen-specific lymphocytes in the peripheral blood of melanoma patients", Nature Medicine, vol. 22, No. 4, Feb. 22, 2016 (Feb. 22, 2016), pp. 433-438.
Bassani-Sternberg et al., "Direct identification of clinically relevant neoepitopes presented on native human melanoma tissue by mass spectrometry", Nature Communications, vol. 7, No. 1, Nov. 21, 2016 (Nov. 21, 2016).

* cited by examiner

CIRCULATING TUMOR CELL ENRICHMENT USING NEOEPITOPES

This application claims priority to our copending U.S. Provisional Patent application Ser. No. 62/512,571, which was filed May 30, 2017.

FIELD OF THE INVENTION

The field of the invention is isolation or enrichment of tumor cells using neoepitopes and validation of immune therapies targeting the neoepitopes, particularly as it relates to circulating tumor cells.

BACKGROUND

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

During the mid-twentieth century, studies conducted by several research teams suggested that tumor cells possessed unique markers. In particular, it was shown that mice could become resistant to a specific carcinogen-induced tumor, while not becoming resistant to other tumors (see, Gross, *Cancer Res.* (1943) 3(5):326-333; Foley, *Cancer Res.* (1953) 13(12):835-837; Prehn et al., *J. Natl Cancer Inst.* (1957) 18(6):769-778; Old, *Natl Cancer Inst Monogr.* (1982) 60:193-209).

Over the next several decades, advances in molecular and cell biology identified specific molecules associated with antigen presentation, including the major histocompatibility complex (MHC). In conjunction with these advances, other technologies were developed that allowed the propagation of various types of immune cells, including cytotoxic T lymphocytes, in cell culture (see, Gubin et al., *J. Clin Invest.* (2015) 125(9): 3413-3421).

Further studies showed that human T cells predominantly reacted with tumor cells but not normal cells, suggesting that human cancers either displayed tumor specific markers or markers that were expressed at lower levels in normal tissues (see, Gubin et al., supra.). These advances suggested that human cancers possessed specific protein sequences that might be targeted for therapeutic treatment. However, identifying these specific sequences remained elusive.

These early studies prompted extensive research to identify cancer-specific molecules. While this line of investigation successfully identified molecules that were overexpressed or underexpressed in various tumors/cancers, these studies were not highly successful in identifying truly cancer specific molecules (see, Srivastava, *Cancer Immunol. Res.* (2015) 3(9): 969-977). Although therapeutic monoclonal antibodies were developed that bound to epitopes expressed on cancer cells, these same targets often were shown to be expressed at lower levels on normal cells. Clinical trials based on markers displayed in both cancerous and non-cancerous cells have response rates typically ranging from 3-20% and often revealed significant toxicity effects (see, Heemskerk et al., *EMBOJ.* (2013) 32:194-203). Nevertheless, such non-specific therapeutic treatments are commonly used today, despite patients often experiencing undesirable side effects due to lack of specificity (see, Srivastava supra).

Recent advances in high-throughput sequencing and bioinformatics have allowed the identification of mutations in cancer cells on an unprecedented scale. This technology has allowed hundreds, if not thousands, of cancer genomes to be sequenced. These cancer genome sequences can be compared with normal genomes to determine the presence of protein-changing mutations. Various studies have shown that tumorigenic/cancerous cells contain tens to hundreds, and in some cases, thousands of somatic mutations (see, Heemskerk supra). At least some of these mutations may result in neoantigens, which are newly formed antigens that have not previously been recognized by the host immune system.

Neoantigens typically arise as a result of the large number of protein-changing somatic cell mutations in tumorigenic cells, and therefore, are tumor- and patient-specific. Some of these mutations are expressed and displayed on the cell surface while other mutations are displayed as peptides bound to MHC molecules on the surface of the tumorigenic cell, providing a unique marker to the tumorigenic cell. The specificity of neoantigens confers a variety of potential advantages for therapy, as compared to self-antigens that may be over- or under-expressed in tumors. For example, because neoantigens are not present in normal cells of the human body, immune system tolerance resulting from mechanisms of central T cell tolerance is minimized. Further, the uniqueness of the neoantigen sequences means that selecting neoantigens as therapeutic targets potentially minimizes autoimmune toxicity and other deleterious side effects. Accordingly, unlike self-antigens, which may be expressed on normal tissues, cells, and organs, neoantigens are expressed only on tumorigenic/cancerous cells and remain an attractive target for new cancer therapies.

Despite these advances, the question remains as to how best to use sequencing information to identify those mutations that have the ability to induce a tumor specific T cell response out of the thousand or so mutations in a tumor cell. While more recent studies (see, Lennerz, *Proc. Nat'l Acad. Sci. USA* (2005) 102:16013-16018) have analyzed large sets of neoantigens in an attempt to identify which neoepitopes are capable of triggering a targeted immune response, this approach is problematic. One issue is that not all neoepitopes will bind to MHC molecules, and thus, not all neoepitopes are capable of being presented on the surface of a cell (see, Heemskerk supra).

This problem is further confounded by Human Leukocyte Antigen (HLA) gene complex diversity, or polymorphisms, present within individual patients. The HLA gene complex, present on chromosome 6p21 and comprising hundreds of different genes, encodes for MHC class I and MHC class II molecules involved in the display of neoepitopes on the surface of the cell and the activation of an immune response. The HLA gene complex includes MHC class I genes, e.g., HLA-A, HLA-B and HLA-C, and MHC class II genes, e.g., HLA-DM, HLA-DO, HLA-DP, HLA-DQ, and HLA-DR. HLA genes are highly polymorphic—for example, more than 12,000 class I alleles and more than 4,000 class II alleles are known (www.ebi.ac.uk/ipd/imgt/hla/stats.html). Such diversity makes it difficult to predict which neoepitopes will trigger an immune response in a particular individual. For example, two individuals, each having different class I alleles, may produce different MHC class I molecules that bind to different neoepitopes. Thus, while the discovery of a large number of mutations within cancer cells provides a potentially unlimited number of therapeutic targets for the treatment of cancer, the problem still remains of how best to determine which of these mutations correspond to neoepitopes that are successfully displayed on the surface of the tumorigenic cell.

Given the enormous diversity of neoepitopes, particularly in combination with patient HLA gene complex diversity, existing models of neoepitope-based treatments have uncertainties with respect to efficacy and patient outcome. Unlike conventional chemotherapeutic treatments, in which techniques for determining efficacy of the treatments are often performed (e.g., using in vitro methods or using a severe combined immunodeficiency (SCID) mouse model), systems and methods for testing efficacy of patient- and tumor-specific immune therapy generally are not known.

In addition, even where transcriptomics data are employed in selecting potential targets for immune therapy, the correlation between transcription and translation is often less than straightforward (see e.g., *Nat Rev Genet.* 2012 Mar. 13; 13(4):227-32). Indeed, post-translational events such as alternative splicing, exclusion of regulatory elements, depletion of ternary complexes, and even protein modification all may lead to low protein levels or even no protein expression at all.

Thus, even though various systems and methods of immune therapy for many cancers are known in the art, all or almost all of them suffer from several drawbacks. Therefore, there is still a need to provide improved systems and methods to more accurately predict the likelihood of success of immune therapy using patient- and tumor-specific neoepitopes.

SUMMARY OF THE INVENTION

Systems and methods are provided for isolation or enrichment of tumor cells, such as circulating tumor cells (CTCs), using neoepitopes and validation of neoepitope-based treatments.

In one aspect, a method of validating immune therapy comprises: (1) generating a synthetic neoepitope peptide using neoepitope sequence data obtained from sequencing the tumor; (2) generating a synthetic antibody that binds to the synthetic neoepitope peptide; (3) contacting a bodily fluid of the patient with the synthetic antibody under conditions that allow binding of the synthetic antibody to a cellular component in the bodily fluid; and (4) detecting the synthetic antibody bound to the cellular component.

In another aspect, the method comprises: (1) using a synthetic antibody against a tumor- and patient-specific neoepitope to enrich or isolate a cellular component in a bodily fluid of the patient; (2) exposing the cellular component to a modified immune competent cell that expresses a chimeric protein or is coupled to an antibody, wherein the chimeric protein or antibody specifically binds the tumor- and patient-specific neoepitope; and (3) detecting an immune response of the modified immune competent cell.

In another aspect, the method comprises: (1) using a synthetic antibody against a tumor- and patient-specific neoepitope to enrich or isolate a cellular component in the bodily fluid of the patient; (2) exposing the cellular component to a chemotherapeutic drug; and (3) detecting an effect of the chemotherapeutic drug on the cellular component.

In another aspect, the method comprises: (1) contacting a bodily fluid of the patient with a synthetic antibody under conditions that allow binding of the synthetic antibody to a cellular component in the bodily fluid, wherein the synthetic antibody specifically binds a patient- and tumor-specific neoepitope of the patient; and (2) detecting the bound synthetic antibody on the cellular component.

In another aspect, the method comprises: (1) using a synthetic antibody against a tumor- and patient-specific neoepitope to enrich or isolate a cellular component in the bodily fluid of the patient; (2) exposing the cellular component to a plurality of immune competent cells of the patient under conditions to stimulate an immune response; and (3) detecting the immune response of the immune competent cells.

Various objects, features, aspects and advantages of the inventive subject matter will become more apparent from the following detailed description of preferred embodiments.

Definitions

As used herein, "administration" refers to the administration of a composition to a patient in need thereof. Administration may occur by any suitable route, including but not limited to, bronchial, enteral, intradermal, intra-arterial, intradermal, intragastric, intramedullary, intramuscular, intranasal, intrathecal, intravenous, intraventricular, mucosal, nasal, oral, rectal, subcutaneous, sublingual, topical, tracheal, transdermal, vaginal, and vitrael.

As used herein, "affinity" is a measure of the strength with which a ligand binds to its receptor. In some embodiments, affinity is measured using quantitative assays known to one of skill in the art, e.g., using an ELISA assay.

As used herein, the term "antibody" generally refers to immunoglobulin molecules and immunologically active portions or fragments thereof of immunoglobulin molecules, i.e., molecules that contain an antigen or neoepitope binding site that immunospecifically binds to an antigen (e.g., neoepitope). Unless the context dictates otherwise, the term "antibody" or "antibodies" includes but is not limited to all isotypes and subtypes of antibodies (e.g., IgA, IgD, IgE, IgG, IgM, etc.), any class (e.g., IgG1, IgG2, IgG3, IgG4, IgA1, and IgA2) or subclass of immunoglobulin molecule, as well as all active fragments (having immunological activity) thereof. It is also understood that any heavy chain (e.g., IgA, IgD, IgE, IgG, IgM) may be paired with any light chain (e.g., kappa or lambda forms). In addition, it should be appreciated that the term "antibody" also includes chimeric T cell/antigen receptors in which the ectodomain includes the antigen or neoepitope binding site of an antibody (e.g., scFv or CDRs from IgG).

Antibodies also include, but are not limited to, monoclonal antibodies, polyclonal antibodies, human antibodies, humanized antibodies, murine antibodies, conjugated antibodies (e.g., to a chemotherapeutic agent, to a radionuclide, to another protein, etc.), synthetic antibodies, bi-specific antibodies, diabodies, chimeric antibodies, single chain antibodies, antibody fragments produced by a Fab expression library, and antibody fragments produced by mRNA display or phage display. Antibodies also include but are not limited to monovalent immunoglobulins (e.g., IgG), and fragments, e.g., $F(ab')_2$, $Fab_2$, Fab', Fab, Fv, single-chain Fv (scFv), scFv-Fc, VhH, disulfide-linked Fvs (sdFv), etc. or any active fragment thereof.

As used herein, "cellular component" of a bodily fluid includes cells or membranous cell-derived entities present in bodily fluid. In some embodiments, the cellular component comprises cells displaying the neoepitope on their surface via a MHC molecule, cellular compartments comprising the neoepitope, or membranous cell-derived entities coupled to the neoepitope. Examples of cellular components include but are not limited to, a circulating tumor cell, a metastatic cell, a circulating microvesicle, a circulating exosome, or a membrane fragment.

As used herein, "composition" or "pharmaceutical composition" refers to a formulation comprising an active ingredient (e.g., an antibody, a checkpoint inhibitor, etc.) and may include one or more additional ingredients (e.g., buffers, excipients, stabilizers, diluents, emulsifiers, preservatives, etc.).

As used herein, and unless the context dictates otherwise, the term "coupled to" or "coupled with" includes both direct coupling (in which two elements that are coupled to each other contact each other) and indirect coupling (in which at least one additional element is located between the two elements). Therefore, the terms "coupled to" and "coupled with" are used synonymously.

As used herein, "human" antibodies refer to antibodies having the amino acid sequence of a human immunoglobulin. Human antibodies include antibodies that are isolated from human immunoglobulin libraries or from animals transgenic for one or more human immunoglobulins and that do not express endogenous immunoglobulins (see, e.g., U.S. Pat. No. 5,939,598). As used herein, "humanized" antibodies refer to antibodies that retain certain antigen binding properties but are less immunogenic, especially with regard to administration to a human patient. For example, humanization by CDR grafting involves transferring the CDRs of a non-human antibody that binds to the target of interest into a human backbone.

As used herein, "immune therapy" includes any and all manners of utilizing a patient's immune system to recognize and destroy cancer cells (e.g., using cells of the immune system, including cytotoxic T cells, CD4$^+$ T cells, dendritic cells, NK cells, and chimeric antigen receptor (CAR) T cells, macrophages, dendritic cells, monocytes, neutrophils, basophiles or eosinophils, B cells, unmodified or modified cells of the immune system, or other components such as antibodies, cytokines, checkpoint inhibitors, etc.). Modified immune cells are cells that have been genetically altered, e.g., a CAR T cell, to recognize an antigen (e.g., a neoantigen). Immune competent cells include cytotoxic CD8$^+$ T cells, CD4$^+$ T cells, dendritic cells, NK cells, and chimeric antigen receptor (CAR) T cells, macrophages, dendritic cells, monocytes, neutrophils, basophiles or eosinophils, B cells, unmodified or modified cells of the immune system, exhausted immune competent cells. In some cases, immune competent cells are obtained from a white blood cell fraction of a patient, e.g., the same patient as from which the tumor is obtained. Any of these cells may be genetically modified to optionally express a recombinant co-stimulatory molecule (e.g., such as a cytokine). Unmodified cells are the native immune cells of the patient.

As used herein, a "matched normal control" refers to a substantially non-diseased biological sample (e.g., blood, tissue, fluid, etc.), preferably from the same patient as the tumor. For DNA analysis, a matched normal control may be obtained from a blood sample, a buccal swab or any other non-disease tissue. For expression analysis, a matched normal control is preferably obtained from normal tissue adjacent to and of the same type as the tumor. In some embodiments, the data obtained from analyzing a tumor (e.g., from whole genome sequencing, exome sequencing, transcriptome analysis, proteomic analysis, etc.) is compared to the matched normal control data prior to initiation of patient treatment.

As used herein, "neoantigen" refers to a new antigen, arising as a result of one or more somatic mutations, and unique to a tumorigenic cell. Neoantigens are not found in germline or normal cells. A cancer specific antigen is specific to the tumor/cancer cell and is not found on normal cells. A tumor associated antigen is an antigen that is overexpressed in a tumor/cancer cell as compared to a normal cell.

As used herein, "neoepitope" is a relatively short peptide that binds to a MHC class I or MHC class II molecule for presentation to the immune system, e.g., a CD4$^+$ helper T cell or a CD8$^+$ cytotoxic T-cell. The neoepitope, which is not present within germline or normal cells, is recognized as non-self and therefore has the capacity to trigger an immune response. Thus, a neoepitope is a short sequence of amino acids, e.g., an antigenic determinant, which binds to a MHC molecule for subsequent presentation to a T cell to trigger an immune response.

In general, neoepitopes are derived from neoantigens, with a neoantigen comprising one or more neoepitopes. For example, neoantigens may be degraded by the proteasome to form a plurality of neoepitopes. The optimal length of the neoepitope will depend upon whether the neoepitope binds to a MHC class I or a MHC class II molecule. In general, neoepitopes may range from 2 to 50 amino acids, as well as any length in between. Additional examples of neoepitope lengths are provided throughout this disclosure. In a preferred embodiment, the mutation(s) in a neoepitope are located centrally relative to the center amino acid position of the neoepitope.

As used herein, "omics analysis" refers to any type of analysis geared towards collectively characterizing and/or quantifying large pools of biological molecules in order to understand the structure, function and dynamics of an organism, biological process, or disease. Types of omics analysis include but are not limited to whole genome sequencing, exome sequencing, transcriptome analysis, proteomics, metabolomics, etc.

As used herein, "specifically binds" refers to non-covalent interactions between a target entity (e.g., a neoepitope) and a binding agent (e.g., an antibody, a T-cell, a MHC complex, etc.), and usually refers to the presence of such an interaction with a particular structural feature (e.g., such as an antigenic determinant) of the target entity with the binding agent. As understood by one of skill in the art, an interaction is considered to be specific if the binding agent binds to the target entity with an affinity of equal or less than $K_D$ 10$^{-8}$ M. Most typically, binding to non-target entities will be at an affinity of equal or more than $K_D$ 10$^{-5}$ M.

As used herein, "synthetic antibody" refers to an antibody that is generated in vitro and is not isolated from an animal after immunization. For example, synthetic antibodies that bind to a synthetic neoepitope peptide may be generated from phage display or mRNA display. The term synthetic antibody as used herein refers not only to immune globulins and fragments thereof, but also to binding entities that are derived from an affinity selection and/or maturation process (e.g., from mRNA display or phage display). For example, scFvs or fragments thereof (e.g., including the complementarity determining regions (CDRs)) responsible for specifically binding to the synthetic neoepitope peptide may be incorporated into an antibody backbone or scaffold, e.g., to generate a full length antibody having specificity for the synthetic neoepitope peptide. In some embodiments, the synthetic antibody is specific for the synthetic neoepitope peptide against which it is generated, as well as for the neoepitope exposed on the surface of the tumor cell. In other embodiments, the synthetic antibody is specific for a neoepitope/MHC complex.

As used herein, "synthetic neoepitope peptide" refers to a synthetic peptide having the same amino acid sequence (or at least 80% or greater sequence identity) as the neoepitope displayed (or predicted to be displayed by in silico methods) on the surface of a tumorigenic cell. In some embodiments, the synthetic neoepitope peptide is utilized in phage display or mRNA display to generate a synthetic antibody that specifically binds to the synthetic neoepitope peptide, and therefore, also binds to the neoepitope displayed on the surface of the tumor cell. Synthetic neoepitope peptides can be produced by solid state synthesis, e.g., Merrifield synthesis.

As used herein, "tumor" or "tumorigenic" refers to cell(s) having uncontrolled, usually rapid, cellular proliferation. Tumors may be benign or malignant, while cancer cells are always considered to be malignant.

As used herein, "therapeutically effective amount" refers to administration of a pharmaceutical composition according to a dosage amount and/or a dosage regimen sufficient to treat a specific disease. For example, as described herein, a therapeutically effective amount of an antibody is an amount of an antibody that is sufficient to ameliorate symptoms associated with a tumor or with cancer, to prevent or delay the growth of the tumor or onset of the cancer, or to lessen the severity or frequency of symptoms of the tumor or of cancer. One of ordinary skill in the art will appreciate that a therapeutically effective amount or dose may depend on a variety of factors, including the type of tumor or cancer, the route of administration of the therapeutic composition, the characteristics of the patient, the extent to which the tumor or cancer has metastasized, and/or the clinical judgment of the health practitioner. Effective doses may also be extrapolated from dose-response curves derived from in vitro or animal model test systems.

Figure 1:
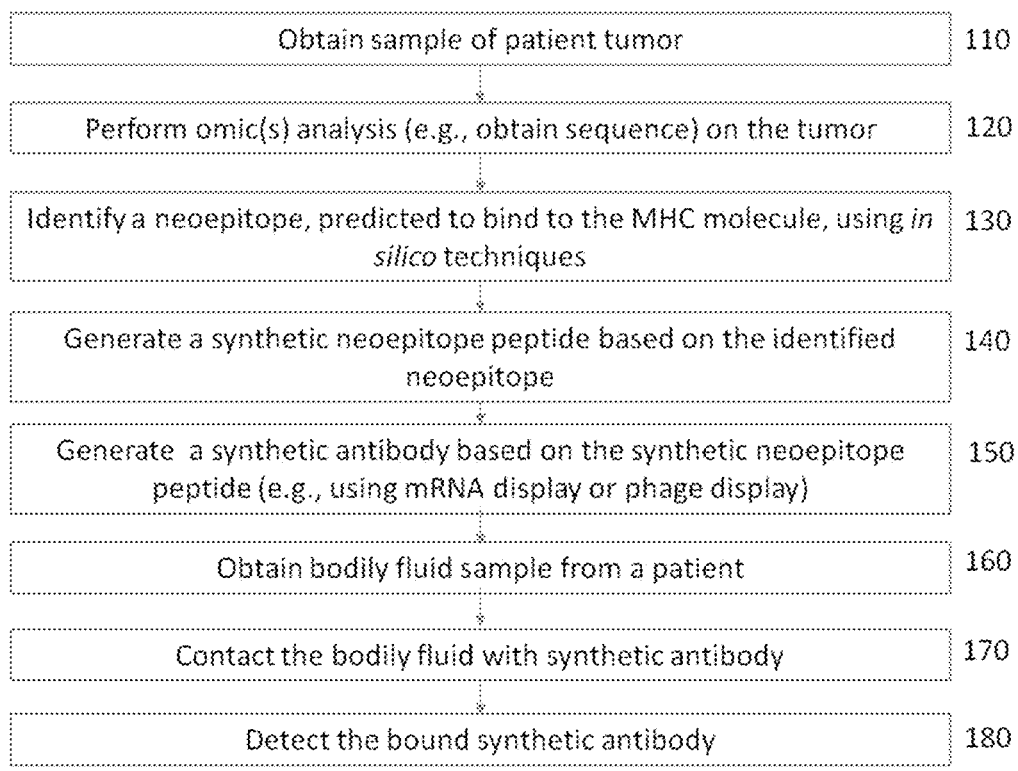
FIG. 1 shows a flow chart describing an exemplary embodiment of the techniques presented herein.

The examples presented herein are not intended to be limiting. It is understood that many different variations of these examples are disclosed within the application, and that all such embodiments fall within the scope of the inventive embodiments.

DETAILED DESCRIPTION

Compositions, systems, and methods are provided for obtaining various tumor cells and/or tumor cell components (e.g., circulating tumor cells (CTCs)) from a patient, especially for validating potential cancer treatment(s) that target one or more patient- and tumor-specific neoepitopes. With this information, therapies can be designed and validated that are specific to the individual with minimal side effects.

The techniques presented herein generally do not rely on obtaining (repeated) biopsies of a tumor of a patient. Once an omics analysis has been performed on the tumor or a cancer cell, this information can be used to derive potential therapies, which are then validated using bodily fluids (e.g., a blood sample). Furthermore, the techniques presented herein can also be performed prior to treatment or during treatment. In still other embodiments, if a proposed or ongoing treatment fails to show efficacy, a different treatment can be selected based on the information obtained from omics analysis (e.g., identification of neoepitopes) and/or from an assay associated with a tumor cell.

Neoantigens and Neoepitopes

Tumor cells contain anywhere from a few to about a thousand somatic mutations (see, Fritsch, *Cancer Immunol. Res.* (2014) 2(6): 522-529). These somatic mutations may lead to the generation of novel sequences, referred to as neoantigens, which are typically not present in germline or normal cells. Thus, neoantigens are specific to the tumor cells and patients from which they originate.

Somatic mutations may arise from a variety of different types of mutations, including nucleotide substitutions (e.g., single nucleotide variants (point mutations)), copy number alterations, DNA rearrangements, transitions, transversions, indels (insertions and/or deletions), amplifications, fusion/translocation events, and any other alternations in the germline sequence that result in novel amino acid sequences or codons. With regard to protein expression, such mutations can lead to non-sense mutations resulting in stop codons, missense mutations resulting in encoding of different amino acids at particular locations, or frame shifts with regard to protein translation. These errors in amino acid sequence can lead to non-functional proteins or proteins with altered functional properties.

Somatic mutations may be trunk mutations or branch mutations. Trunk mutations are present in the majority of tumor cells. Branch mutations are present in subclonal populations of the tumor cells.

Somatic mutations may be classified as driver mutations or passenger mutations. Driver mutations include those mutations that confer growth advantages to tumorigenic/cancer cells. Passenger mutations include those mutations that have not conferred a growth advantage to tumorigenic/cancerous cells, but are present in the population of tumorigenic/cancerous cells.

It is understood that the techniques presented herein are applicable to any type of tumor, including but not limited to, primary tumors (e.g., the original tumor), secondary tumors (e.g., tumors of the same type as the original tumor but present in a different location of the body), recurrent tumors (e.g., reappearance(s) of the primary or secondary tumor), and derivative tumors (e.g., a primary or secondary tumor that has acquired additional mutations).

According to the present disclosure, neoantigens may comprise one or more neoepitopes. In some embodiments, neoepitopes that bind to MHC class I molecules are typically 9 amino acids in length, while neoepitopes that bind to MHC class II molecules are typically about 14 to 20 amino acids in length. In other embodiments, neoepitopes that bind to MHC class I molecules are typically about 7 to 12 amino acids in length, while neoepitopes that bind to MHC class II molecules are typically about 15 to 25 amino acids in length. It should be noted that neoepitopes as used herein are characterized as random mutations or pattern-type mutations in tumor cells that give rise to unique and tumor specific antigens with respect to a given patient.

To trigger a T cell response, neoepitopes need in most cases to bind to two domains, e.g., the MHC domain and the T cell receptor domain. Thus, a neoepitope will have specified amino acid residues at specific positions, referred to as anchoring residues, that result in binding or anchoring of the neoepitope to the MHC. For MHC class I molecules, it is understood that these anchoring residues may vary depending upon the specific HLA alleles possessed by the patient. Similarly, for MHC class II molecules, it is understood that these anchoring residues may vary depending upon the specific HLA alleles possessed by the patient. Thus, the same neoepitope may bind to a MHC class I or class II receptor in one patient, but may not bind to a MHC class I or class II receptor in another patient having different HLA alleles.

Neoepitopes arising from somatic mutations are primarily displayed via the MHC class I pathway. This pathway targets intracellularly derived mutant sequences such as neoantigens/neoepitopes. However, it is understood that in the context of therapeutic applications (particularly immunotherapy), and as described in additional embodiments throughout this application, the neoepitopes presented herein can be used to trigger immune responses in both MHC class I and MHC class II pathways. For example, for a neoepitope to activate a MHC class II pathway, in one embodiment, synthesized neoepitope peptide(s) may be injected, endocytosed, and processed for presentation (e.g., involving binding to a MHC class II molecule on the surface of the cell). Alternatively, cytoplasmic and nuclear antigens can be engulfed by autophagy and processed according to a MHC class II pathway. In still other embodiments, an antigen presenting cell (APC) may exhibit cross-presentation, e.g., by presenting exogenous antigens with MHC class I molecules. In still other embodiments, expressed recombinant neoenatigens/neoepitopes may be trafficked to the endosomal or lysosomal compartments, leading to preferential MHC-class II presentation.

A neoepitope will in most cases also have specified amino acid residues at other designated positions, referred to as T cell binding residues, which result in binding or anchoring of the neoepitope to the T cell, e.g., a CD8+ T cell or CD4+ T cell. Similarly, the amino acid residues that interact with the T cell receptor may also vary from patient to patient, based on the diversity of T-cell receptors (e.g., allelic sequence variation within the T cell receptor (TCR) loci) of the patient.

There are multiple mechanisms which may facilitate triggering of an immune response by a neoepitope. In some embodiments, the neoepitope may have an increased binding affinity to the MHC complex as compared to its non-mutated counterpart. In other embodiments, the neoepitope may bind to the T-cell receptor with an increased binding affinity as compared to its non-mutated counterpart. In still other embodiments, the neoepitope may undergo a structural change as compared to its non-mutated counterpart, which facilitates binding to the T-cell receptor and/or MHC molecule. Other mechanisms are possible, and all such mechanisms are contemplated herein.

An advantage to neoepitope based therapies is that these sequences are specific to tumor cells, and therefore, limitations present with existing therapies based on self-antigens (e.g., autoimmune toxicity that results in the destruction of healthy tissues, organs and/or cells, or T-cell tolerance in which the immune system fails to recognize the tumor cell) are unlikely to be particularly problematic with these techniques. Additionally, since neoantigens are tumor- and patient-specific, therapies can be personalized to individual patients. By utilizing neoepitopes, patient- and tumor-specific therapies with minimal side effects can be developed.

In some embodiments, the neoepitope has an above-normal expression level as compared to a matched normal control. Expression levels may be quantified by any suitable technique known in the art, including but not limited to, quantitative RNA analysis (e.g., RNA-Seq) or quantitative proteomics analysis (e.g., mass spectrometry). It is also understood that the tumor cells may exhibit altered protein expression of non-mutated proteins, including overexpression or underexpression of non-mutated proteins.

Obtaining a Tumor Sample from a Patient

A tumor sample from the patient may be obtained by any conventional technique, including but not limited to biopsy (e.g., excisional biopsy, incisional biopsy, percutaneous needle biopsy, etc.) or surgical resection, etc. In some embodiments, a biopsy is performed once to obtain patient-specific tumor cells. Once obtained, the cells may be immediately used, propagated in cell culture according to known techniques in the art for immediate use (e.g., omics analysis), or frozen into aliquots for subsequent use. Likewise, biopsy sections may be freshly used or after preservation (cryopreservation or formalin/paraffin embedded).

Various types of information may be obtained from an omics analysis of a tumor sample, as discussed herein. In an embodiment, the tumor is subjected to, e.g., genome or exome sequencing, and the mutational profile of a tumor from a particular patient can be determined. As disclosed herein, the sequence information from the tumor can be compared to a matched normal control or other reference sequence (if a matched normal control is not available) to identify locations of mutations in the tumor genome as well as the mutational load (total number of mutations present).

'Omics' Analysis

In general, it is contemplated that 'omics' analysis includes any one or more of the following: whole genome sequencing (WGS), exome sequencing, RNA expression profiling and/or RNA quantification (RNA-Seq), proteomics analysis, metabolomics analysis, and any other type of analysis in biology used for characterizing large pools of biological molecules.

It is contemplated that genomic analysis can be performed by any number of suitable analytic methods, however, especially preferred are whole genome sequencing (WGS) and exome sequencing of both a tumor and a matched normal control sample. Therefore, common to most analyses is the isolation of nucleic acids for subsequent analyses (e.g., genomic DNA, RNA transcriptome, etc.)

In some embodiments, high-throughput sequencing/next generation sequencing methods according to methods known in the art (see, Reuter, *Mol Cell* (2016) 58(4):586-597) may be used to obtain the WGS sequence of tumor cells and of matched normal control cells. In some embodiments, sequencing will be performed on a large number of cells, however, sequencing may also include single cell sequencing. High throughput sequencing methods may also be utilized to obtain the exome sequence, which represents the coding region of the whole genome (e.g., typically about 1 to 5% of the whole genome). In other embodiments, exome sequencing may also include copy number. It is understood that any suitable sequencing technique may be utilized, including but not limited to massively parallel high throughput sequencing, ion torrent sequencing, pyrosequencing, etc.

In still other embodiments, as an alternative to WGS or exome sequencing, specific regions of the tumor cell may be targeted for sequencing, e.g., in some cases these regions may be known to be associated with tumor or cancer causing mutations. In still other embodiments, these regions may include all genes of a particular type, e.g., all kinase genes (the kinome), etc.

According to the present disclosure, it is contemplated that, prior to treatment, a tumor biopsy and matched normal control (if available) is obtained from a patient, and omics analysis is performed on the obtained tumor and matched normal control sample to identify a population of neoantigens/neoepitopes present within the tumor cells. Thus, in some embodiments, the tumor cells obtained from the biopsy contain anywhere from a few somatic mutations to about a thousand somatic mutations. In some embodiments, the tumor cell contains at least 10 somatic mutations, at least 20 somatic mutations, at least 30 somatic mutations, at least 40 somatic mutations, at least 50 somatic mutations, at least 75 somatic mutations, at least 100 somatic mutations, at least 200 somatic mutations, at least 300 somatic mutations, at least 400 somatic mutations, at least 500 somatic mutations, and so forth, up to about 1000 somatic mutations or more. Since not all somatic mutations result in neoepitopes that are capable of binding to a MHC class I or class II molecule, the total number of somatic mutations in a cell will generally be greater than the number of neoepitopes capable of being displayed on the surface of a tumorigenic/cancerous cell.

Once the sequence of the tumor (e.g., whole genome, exome, or a subset of the genome, etc.) has been obtained, the sequence of the tumor cell can be compared to the sequence of the matched normal control to determine locations and prevalence of mutations. Specifically, the tumor and matched normal control sequences may be aligned to determine the presence and locations of mutations.

The computational alignment and analysis of the sequence data may be performed in a variety of ways. Advantageously, however, analysis is performed in silico by location-guided synchronous alignment of tumor and normal samples as disclosed, for example, in US 2012/0059670A1 and US 2012/0066001A1 using BAM files and BAM servers. Of course, alternative file formats (e.g., SAM, GAR, CRAM, FASTA, etc.) are also expressly contemplated herein. It should be noted that exome and/or high-throughput genome sequencing allows for rapid and specific identification of patient specific neoepitopes, particularly where the analysis also takes into account matched normal controls from corresponding normal tissue of the same patient.

Other types of omics analysis may be performed on the tumor and matched normal control. For example, RNA expression profiling and/or RNA quantification (RNA-Seq) may also be performed on the tumor (in addition to genomic sequencing) to show levels of gene expression of the tumor at a moment in time. RNA sequencing and/or quantification can be performed in all manners known in the art. The RNA expression profile may include one or more of messenger RNA (mRNA), primary transcript RNA (hnRNA), ribosomal RNA (rRNA), transfer RNA (tRNA), microRNA (miRNA), non-polyadenylated RNA, antisense RNA (asRNA), small interfering RNA (siRNA), etc. Specific embodiments include mRNA and hnRNA. The set of expressed genes, also known as the transcriptome, is identified using RNA sequencing and is usually combined with RNA quantification indicating the amount or concentration of each RNA molecule. Identifying the transcriptome is not reliant upon known coding regions, and therefore, can identify novel transcripts, e.g., from intragenic fusions or from tumors.

In other embodiments, RNA-Seq technology may be used. This technology, also referred to as whole transcriptome shotgun sequencing (WTSS) utilizes NGS technology to reveal the presence of expressed sequences along with the quantity of the expressed sequences. RNA-Seq technology does not require species or transcript specific probes, and can detect novel transcripts, gene fusions, single nucleotide variants, indels, and other previously unknown changes difficult to detect with traditional microarray technology.

In still other embodiments, RNA sequence information may be obtained from reverse transcribed polyA$^+$-RNA, which is in turn obtained from a tumor sample and a matched normal (healthy) control sample of the same patient. PolyA$^+$-RNA is typically preferred as a representation of the transcriptome.

Analysis of expression levels can be performed in any manner known in the art and other preferred methods of RNA quantification and sequencing include quantitative PCR (qPCR) and/or real-time PCR (rtPCR)-based methods, although other methods (e.g., solid phase hybridization-based methods) also may be used. Viewed from another perspective, transcriptomic analysis may be used (alone or in combination with genomic analysis) to identify and quantify genes having a cancer- and patient-specific mutation. Other techniques for conducting RNA profiling are well known in the art (see, Vartanian et al., *BMC Genomics* (2009) 10(2): 1-16) and are contemplated herein.

Proteomics analysis, another type of omics analysis, is directed towards identification and quantification of protein expression at a moment in time and can also be performed in numerous manners. However, particularly preferred proteomics methods include antibody-based methods and mass spectroscopic methods (see, Yadav, *Nature* (2014) 515:572-576). In still other embodiments, particularly preferred proteomics methods include selected reaction monitoring. Moreover, it should be noted that proteomics analysis may not only provide qualitative or quantitative information about the protein per se, but may also include protein activity data where the protein has catalytic or other functional activity. Preferred methods include quantitative proteomics analysis. Exemplary techniques for conducting proteomic assays are found in U.S. Pat. Nos. 7,473,532 and 9,091,651. All known methods of performing proteomics analysis are contemplated herein.

Thus, in some embodiments, one or more neoepitopes are detected by whole genome sequencing. In other embodiments, one or more neoepitopes are detected by exome sequencing. In other embodiments, one or more neoepitopes are detected by RNA sequencing. In still other embodiments, one or more neoepitopes are detected by microarray or immunoassay, including ELISA, Western Transfer, or microarray hybridization probes. In other embodiments, one or more neoepitopes are detected by mass spectrometry. In still other embodiments, one or more neoepitopes may be detected by targeted sequencing panels. In yet other embodiments, one or more neoepitopes are detected by DNA-protein interactions (e.g., ChIP-sequencing) and/or epigenome characterization.

As previously mentioned, the computational alignment and analysis of the sequence data may be performed in numerous manners in silico. Any language herein directed to a computer should be read to include any suitable combination of computing devices, including servers, interfaces, systems, databases, agents, peers, engines, controllers, or other types of computing devices operating individually or collectively. Computing devices may contain comprising one or more processors configured to execute software instructions stored on a tangible, non-transitory computer readable storage medium (e.g., hard drive, solid state drive, RAM, flash, ROM, etc.).

The software instructions advantageously configure the computing device(s) to provide the roles, responsibilities, or other functionality as discussed herein with respect to the disclosed systems. Further, the disclosed technologies can be embodied as a computer program product that includes a non-transitory computer readable medium storing the software instructions that cause a processor to execute the disclosed steps associated with implementations of computer-based algorithms, processes, methods, or other instructions. In particular embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network, a circuit switched network, cell switched network, or other type of network.

Additionally, any high throughput computing framework is contemplated herein including, Cluster MapReduce, Apache Spark, High Performance Computing Cluster (HPCC), Hydra, etc. These frameworks provide interfaces and analytics capabilities for processing and analyzing large sets of data.

In some embodiments, the threshold level for inclusion of neoepitopes as a therapeutic target will be an expression level of at least 20%, and more typically, at least 50% as compared to a matched normal control, thus ensuring that the epitope is at least potentially 'visible' to the immune system. (Here, it is understood that the matched normal control does not express the neoepitope, since the neoepitope is unique to the cancer cell. Therefore, the expression level of the neoepitope may be compared to the non-mutated counterpart of the neoepitope, an average gene expression level of the matched normal control, or a median gene expression level of the matched normal control.) Thus, it is generally preferred that the omics analysis also include an analysis of gene expression (transcriptomic analysis) to help identify and characterize the level of expression of the neoepitope. Viewed from another perspective, transcriptomic analysis may be suitable (alone or in combination with genomic analysis) to identify and quantify genes having a cancer- and patient-specific mutation. Numerous methods of transcriptomic analysis are known in the art, and are suitable for use herein. Taking the above into consideration, it should therefore be appreciated that a patient sample comprising DNA and RNA from tumor and matched normal control tissue can be used to identify specific mutations and to quantify expression of such mutations.

In one aspect, tumor-specific neoepitopes are identified against a matched normal control sample of a patient, and preferably subject to further analysis and filtering only if specified criteria, e.g., involving predefined structural and expression parameters, and/or sub-cellular location parameters, are met. For example, in some embodiments, it should be appreciated that neoepitope sequences are only retained provided that these sequences meet a predefined minimum expression threshold (e.g., at least 20%, 30%, 40%, 50%, or higher expression as compared to matched normal control expression). In other embodiments, neoepitopes are only retained if the mutation is due to a missense mutation and/or if expression of the neoepitope is above a minimum expression level as compared to the matched normal. In still other embodiments, filtering can be further refined by confirming a high transmembrane expression level of cancer neoepitopes, e.g., neoantigens having a membrane associated location at the outside of a cell membrane. In still other embodiments, contemplated analyses include structural calculations that delineate whether or not a neoepitope is likely to be solvent exposed, or whether the neoepitope presents a structurally stable epitope, etc. Further examples, methods, and neoepitopes are found in co-pending, co-owned International applications WO 2016/164833 and WO 2016/172722, both incorporated by reference herein. WO 2016/172722 contains a table of neoepitopes, e.g., Table 1, for a variety of cancer types.

As previously indicated, matched normal controls are used whenever possible. As an example, if only the right lung contains a tumor, but the left lung is tumor free, then it is possible to compare the tumor with normal control tissue matched to the same anatomic site (e.g., right and left inferior lobe) from the same patient. Measurements of RNA expression levels from the normal sample can be used to generate a normal expression profile, and the normal expression profile can then be compared to the RNA expression profile of the tumor in order to ascertain differences in RNA expression.

However, in cases where a matched normal control is not available, a database comprising an aggregate of expression levels of normal sequences for a particular cell, tissue, organ, or bodily fluid may be consulted. For example, a database can be accessed to obtain sequences of normal tissue samples from different individuals, e.g., matched to the same anatomic site as the tumor as well as expression profiles. These normal expression profiles can be aggregated and compared to the RNA expression profile of the tumor in order to ascertain differences in RNA expression.

Neopeptide and MHC Analysis

As immunotherapy treatment success requires, inter alia, neoepitopes to be presented via the MHC complex, it should be appreciated that the neoepitopes or their precursors must not only be suitable for intracellular processing via appropriate mechanisms (e.g., proteasomal cleavage, formation of a TAP complex, vesicular transport, etc.) but also must have a minimum affinity for the MHCs as determined by a patient's particular HLA-type. In other embodiments, the neoantigen/neoepitope may also be presented on the outside of the cells, for example, as part of a transmembrane or membrane bound extracellular protein. Such neoantigens or neoepitopes may be subject to antibody recognition and immune response by NK cells recognizing a bound antigen.

For the purposes of this disclosure, it is understood that the neoepitope sequence data from omics analysis can be used to generate a pool of candidate neoepitopes having somatic mutations. However, it is not known whether these candidate neoepitopes are actually displayed on the surface of the tumorigenic cell. Not all of these mutations will appear as neoepitopes presented in conjunction with an MHC molecule or will be displayed as part of a neoantigen on the cell surface (e.g., for binding by an antibody or a T cell receptor). For a neoepitope to appear on the cell surface as part of its corresponding neoantigen, the neoantigen must be of a sufficient length and have characteristics suitable for embedding in the cell membrane (e.g., a transmembrane domain), and additionally, the neoepitope must be exposed, and not buried in the interior of the neoantigen for an antibody to bind to the exposed neoepitope. In other cases, for an immune response to be triggered, the neoepitope should also be capable of binding to a MHC class I or class II molecule for a patient's T cell receptor or a modified T cell receptor to bind to the complexed neoepitope. Thus, in some embodiments, neoepitopes are selected at least in part based on predicted ability to bind to a MHC complex or to be exposed on the cell surface. In other embodiments, and as described throughout, detection of neoepitope/MHC complexes are also possible, and in these cases, neoepitopes may be selected primarily based on predicted ability to bind to an MHC complex. Computational methods may be employed to address these types of questions.

To facilitate computational identification of neoepitopes, it is contemplated that candidate neoepitopes will be confined to relatively small fragments capable of MHC binding. In some embodiments, the candidate neoepitopes will be generated from neoantigens, with each candidate neoepitope being between about 5-25 amino acids, and in some cases longer, e.g., about 2-50 amino acids. Thus, for MHC class I binding, suitable candidate neoepitopes may preferably have a length of between 5-12 amino acids, 7-11 amino acids, 8-10 amino acids, or 9 amino acids, including the mutated amino acid. In other embodiments, for MHC class II type binding, suitable candidate neoepitopes may preferably have a length of between 12-22 amino acids, 14-20 amino acids, 15-25 amino acids, or 16-20 amino acids, including the mutated amino acid. In some embodiments, candidate neoepitopes comprising single nucleotide variants are selected and screened for their ability to bind to a MHC molecule.

In some embodiments, once the total population of candidate neoepitopes has been determined, the candidate neoepitopes are analyzed by software such as NetMHC (see, Fritsch, *Cancer Immunol. Res.* (2014) 2(6): 522-529) to predict or identify which candidate neoepitopes are most likely to bind to MHC class I molecules. In order for a neoepitope to be displayed on the surface of a cell as a MHC class I/neoepitope complex, the neoepitope needs to be capable of binding to a MHC class I molecule. Not all neoepitopes are capable of binding to a MHC, and therefore, software programs such as NetMHC can be used to predict which sequences (analysis is based on sequence information and predicted binding affinity) should be prioritized as potential therapeutic or diagnostic targets. (It is noted that NetMHCII is available for prediction of neoepitopes that bind to MHC class II molecules.) The candidate neoepitopes with predicted high affinity are more likely to be displayed complexed with the MHC molecule on the surface of the cell, provided that these candidate neoepitopes are able to be processed and transported by the cellular machinery. Accordingly, candidate neoepitopes from this group can be selected as targets for synthetic antibodies as well as for modified T cells.

In addition, additional filtering may be performed to identify candidate neoepitopes with corresponding neoantigens suitable for display on the cell surface, e.g., such as a transmembrane domain. Here, the goal is to identify neoepitopes that are displayed on the surface of the cell and that are solvent accessible, not buried within the tertiary structure of the neoantigen.

Thus, instead of randomly selecting candidate neoepitopes and generating antibodies against these candidate neoepitopes (i.e., the corresponding synthesized peptide), which may or may not appear on the surface of the cell, in silico prediction programs can be used to identify candidate neoepitopes based on one or more properties, including but not limited to, predicted high affinity to the MHC, solvent accessibility, presence of a nearby transmembrane domain, predicted stability, etc. Identification of candidate neoepitopes can be performed with a single in silico prediction program or a combination of in silico prediction programs. Candidate neoepitopes that have been identified by in silico prediction programs are referred to as in silico identified neoepitopes or identified neoepitopes. In some embodiments, in silico programs utilize neural network and machine learning approaches in conjunction with large training sets of data (e.g., data containing experimentally determined binding affinities of specific peptides to specific MHCs, data listing experimentally determined neoantigens displayed on the surface, etc.), to predict which candidate neoepitopes are optimal, e.g., which bind to MHC molecules with high affinity or any other suitable conditions.

In some embodiments, these software programs may utilize a particular allele, e.g., NetMHC utilizes a well characterized allele, HLA-A0201, to make binding predictions. In other embodiments, the in silico software program is provided with the sequence of the patient's HLA or with information identifying the patient's type of HLA (allele). Therefore, it is generally preferred that the HLA type of the patient be determined, using conventional wet-lab methods or by in silico techniques. Viewed from a different perspective, it should be appreciated that in silico identified neoepitopes may be further qualified for prediction of treatment outcome by ascertaining their binding to the patient specific MHC-type.

Thus, software programs may make predictions of affinity based on the sequence of the candidate neoepitope, sequence of the patient's MHC, and experimentally determined binding affinities from test data sets. As previously mentioned, for a given candidate neoepitope, certain residues are anchor residues that anchor the sequence to the MHC class I or class II molecule. For most MHC molecules, there are typically between one and three anchor positions, and usually one to three amino acids at each anchor position that promote binding. Thus, based upon this information and using in silico methods, affinity may be predicted using programs such as NetMHC. Other in silico programs such as ANN-Hydro utilize neural networks and machine learning to predict immunogenic epitopes, e.g., based on the presence of hydrophobic amino acids at certain positions (e.g., T-cell receptor contact residues within epitopes) as well as other factors (Chowell, D. PNAS (2015) E1754-1762).

Any MHC binding prediction program may be utilized, including but not limited to, NetMHC, NetMHCII, NetMHCpan, MAPPP/BIMAS, ANN-Hydro, and RANK-PEP or other custom software (Segal, N. et al., Cancer Res. (2008) 68(3):889-92).

While these prediction algorithms perform reasonably well with regard to binding of a candidate neoepitope to a MHC complex, these algorithms cannot predict with certainty that the in silico identified neoepitope(s) will be expressed and displayed on the surface of the tumor cell. These prediction programs generally operate based off genomic DNA (instead of RNA expression levels or protein expression levels), and accordingly, do not account for the various ways that the neoepitope can be destroyed (e.g., by the proteasome, by loss of function of the tumor cell to display neoepitopes attached to MHC molecules, by failure to express the neoepitope, etc.). It is contemplated that experimental validation is needed in order to determine whether an identified epitope is presented on the surface of a cell, and whether that identified neoepitope can trigger an immune response.

For MHC class I pathways, once a neoantigen is degraded into smaller fragments by the proteasome, the peptides (neoepitopes) are transported by the TAP transporter into the ER. The TAP transporter is found in the endoplasmic reticulum (ER) lumen and mediates transport of peptides into the ER for processing. Once delivered into the ER, the neoepitope binds to the MHC class I molecule and is transported through the Golgi apparatus and delivered to the cell surface for display. MHC class I molecules bind to epitopes originating from within the cell. Thus, it is contemplated that neoepitopes are largely processed according to MHC class I pathways. In other embodiments, APCs such as dendritic cells may exhibit cross-presentation, e.g., by presenting extracellular antigens with MHC class I molecules.

For MHC class II processes, neoantigens external to the cell are endocytosed and degraded in endocytic vesicles, which join with vesicles containing MHC class II molecules. Here, a neoepitope binds to a MHC class II molecule, and is transported to the cell surface for display. MHC class II molecules bind to foreign epitopes originating from outside the cell. Thus, it is contemplated that the MHC class II pathway could be activated by injecting a synthetic neoepitope peptide (e.g., an in silico identified neoepitope that has been synthesized) into a patient, wherein the synthetic neoepitope peptide would be processed according to MHC class II pathways and displayed on the surface of the cell. In still other embodiments, APCs such as dendritic cells may exhibit cross-presentation, e.g., by presenting extracellular antigens with MHC class I molecules. Alternatively, cytoplasmic and nuclear antigens can be engulfed by autophagy and processed according to a MHC class II pathway.

Thus, with these processes in mind, the pool of potential/candidate neoepitopes obtained from omics analysis may be further reduced by algorithms that identify sequences that are not compatible or less compatible with the cell's machinery. For example, neoantigens that are predicted to be resistant to proteasome degradation can be identified and excluded, as these molecules would not be expected to be processed and displayed on the cell surface. In other examples, neoepitopes corresponding to neoantigens that are predicted not to be displayed on the cell surface or are buried in a hydrophobic pocket can be excluded. As another example, the pool of candidate neoepitopes may be further reduced by algorithms that identify peptide fragments that are not able to be transported into the ER by the TAP transporter. Similarly, candidate neoepitopes may fail to be compatible with other cellular processes regarding processing and display of the neoepitope on the cell surface.

Thus, it is contemplated that candidate neoepitopes that are predicted to be compatible with cellular processes will be identified by in silico methods, and that these identified neoepitopes can undergo degradation, transport, binding and any other processing in order to be displayed on the surface of the cell, e.g., as part of a MHC complex. In some embodiments candidate neoepitopes may be additionally screened based upon hydrophilicity and projected stability. These candidate neoepitopes are also selected based on their ability to bind to a MHC molecule.

In other embodiments, if RNA expression data is available, then the pool of candidate epitopes may be refined by selecting those candidate neoepitopes that are overexpressed.

HLA gene complex determination can be performed using various methods of wet-chemistry that are well known in the art, and all of these methods are deemed suitable for use herein. However, in especially preferred methods, the HLA-type can also be predicted from omics data in silico using a reference sequence containing most or all of the known and/or common HLA-types. In short, a patient's HLA-type is ascertained (using wet chemistry or in silico determination), and a structural solution for the HLA-type is calculated or obtained from a database, which is then used as a docking model in silico to determine binding affinity of the candidate neoepitope to the HLA structural solution. Suitable in silico prediction methods of the HLA-type of a patient especially include those described in co-pending, co-owned U.S. provisional application 62/209,858 (filed 25 Aug. 2015), which is incorporated by reference herein. Suitable systems for determination of binding affinities include the NetMHC platform (see e.g., Lundegaard C., *Nucleic Acids Res.* (2008) Jul. 1; 36(Web Server issue): W509-W512). Candidate neoepitopes with high affinity (e.g., less than 500 nM, less than 200 nM, less than 100 nM, less than 75 nM, less than 50 nM) against the previously determined HLA-type are then identified.

Once patient- and tumor-specific candidate neoepitopes and HLA-type are identified, computational analysis can be performed by docking candidate neoepitopes to the MHC complex and determining the best binders (e.g., lowest $K_D$, for example, less than 50 nM) or binders with a desirable affinity range (e.g., $K_D$ between 50 nM and 500 nM, or between 100 nM and 300 nM, or between 200 nM and 400 nM, or between 100 nM and 500 nM). It should therefore be appreciated that such an approach identifies neoepitopes that are most likely to be presented on a cell surface with a MHC molecule and as such are most likely to elicit an immune response with a therapeutic effect.

It is understood that many wet-chemistry techniques are known in the art for HLA determination, and that these technique are within the scope of the embodiments presented herein.

In practice, neoepitopes can be scored/ranked based on allele frequency multiplied by the transcripts per million number to get a likelihood score. This score can then be further augmented using HLA information and calculated or actual binding affinity to the patient's HLA type. For example, an exemplary ranking format may be:
>254 NM_001000.3 RPL39 Missense p.M29K A->T Normal: WIRMKTGNK, AF: 0.179104477612 TPM: 1023.96 TPM_MEDIAN: 7.35 LL: 183.395820896 netMHC: 242.96 Allele: HLA-A0301 WIRKKTGNK.

Here, the file is a FASTA formatted file, and entries start with the '>' character, which reports sample information. The sample information line contains a number used for indexing the sample (e.g., 254), the Refseq Gene ID (e.g., NM_001000.3), the HUGO common name (e.g., RPL39), the variant classification (e.g., Missense), the protein change (e.g., p.M29K), the base pair change (e.g., A->T), the normal epitope (e.g., Normal: WIRMKTGNK), allele frequency (e.g., AF: 0.179104477612), Transcripts per million for this gene (e.g., TPM: 1023.96), TPM_MEDIAN which is the median expression level of all the genes (e.g., TPM_MEDIAN: 7.35), the LL score which is just AF×TPM (e.g., LL: 183.395820896), the netMHC predicted binding value (e.g., netMHC: 242.96), and the specific HLA allele that the neoepitope binds to (e.g., Allele: HLA-A0301). The next entry is the neoepitope (e.g., WIRKKTGNK).

Thus, it should be recognized that it is feasible to assemble an entire rationally-designed collection of in silico identified neoepitopes of a specific patient with a specific cancer, which can then be further tested in vitro to find or generate high-affinity antibodies that bind to these specific identified neoepitopes. Indeed, contemplated collections may include one, two, three, four, five, six-ten, 10-50, 50-150, 1,000 and even more patient- and cancer-specific identified neoepitopes. Viewed from a different perspective, the rational-designed collection of identified neoepitopes may cover between 1-10%, or between 10-25%, or between 25-60%, or between 60-100% of all neoepitopes that are expressed and bind to the HLA type of the patient. Thus, contemplated collections will comprise at least 15%, at least 25%, at least 50%, at least 70, or at least 90% of the cancer immunome (neoepitopes that are expressed and bind to the HLA type of the patient). Consequently, it should also be appreciated that even for patients with tumor immune suppression or chemotherapy-damaged immune systems, the techniques presented herein provide numerous novel targets for immune therapy.

Identification of the candidate neoepitopes are performed in silico. Once the candidate neoepitopes are identified, therapies can be created which target neoepitopes on the surface of tumor cells. It is contemplated that once the neoepitope(s) have been identified, in vitro generation of synthetic peptides having the neoepitope sequence(s) will be created, and that synthetic antibodies may be generated against these synthetic neoepitope peptides as is discussed in more detail below. It is also contemplated that therapies will be created to target neoepitope(s) displayed on tumor cells. More than one, more typically more than ten, or more than 100 candidate neoepitopes can be synthesized using peptide synthesis. Antibodies can be generated against these synthetic neoepitope peptides and validated experimentally with bodily fluids obtained from the patient where the bodily fluids include one or more cellular components that present the neoantigen or neoepitope. These techniques are discussed in more detail below.

Peptide Synthesis

To obtain a synthetic antibody against the identified neoepitope(s), it is contemplated that the in silico identified neoepitope(s) are prepared in vitro to yield synthetic neoepitope peptide(s) having the same sequence (or greater than 80% sequence identity) as the identified neoepitope(s). Once the synthetic neoepitope peptide (s) are synthesized, antibodies can be generated against the synthetic neoepitope peptide(s). Techniques for synthesizing synthetic neoepitope peptides and generating synthetic antibodies are presented herein. Synthetic neoepitope peptides are also referred to herein as synthetic peptides.

In other embodiments, the synthetic neoepitope peptide(s) may have 80% sequence identity, 85% sequence identity, 90% sequence identity, 95% sequence identity, 96% sequence identity, 97% sequence identity, 98% sequence identity, 99% sequence identity, or 100% sequence identity to the neoepitope on the tumor cell. In some embodiments, the sequence of the synthetic neoepitope peptide is homologous (or has 80% sequence identity, 85% sequence identity, 90% sequence identity, 95% sequence identity, 96% sequence identity, 97% sequence identity, 98% sequence identity, 99% sequence identity) as compared to neoepitope sequence data used in generation of an immune therapeutic (e.g., the expression system for expression of the neoepitope in a patient cell line or chimeric antigen receptor in a cytotoxic cell).

There are numerous methods known in the art to prepare synthetic peptides, and all known manners are deemed suitable for use herein. Solid-phase peptide synthesis, a well-developed and characterized technology for protein synthesis, is used in a preferred embodiment. For example, synthetic peptides with cancer neoepitope sequences can be prepared on a solid phase (e.g., using Merrifield synthesis, also referred to as solid-phase peptide synthesis). According to certain embodiments, solid phase synthesis of peptides involves attaching an initial (primary) amino acid to a solid surface and adding additional amino acids in a step-wise manner to form a peptide chain.

In general, this technique may be used to synthesize amino acids chains from two to about 100 residues. In some embodiments, a linker or spacer may be present between the solid surface and the primary amino acid. In other embodiments, the amino acid chains may optionally include unnatural amino acids, chiral peptides or other modifications to the peptide/protein backbone.

Reaction cycles in solid-phase peptide synthesis generally involve a series of reaction steps including a deprotection step, a wash step, a coupling step, and another wash step. Since the peptide is attached to the solid surface, by-products, excess reagents and other contaminants may be rinsed away while retaining the surface-attached peptide chain.

It is desirable that each step of solid phase synthesis result in a high yield, e.g., greater than 95%, 96%, 97%, 98%, or 99% yield. Solid phase peptide synthesis may be performed manually, or alternatively, may be performed by an automated synthesizer. Solid phase peptide synthesis conventionally proceeds in a C-terminal to N-terminal manner, in an opposite direction to that of ribosome protein synthesis.

Solid surfaces include any solid material to which an amino acid may be attached (e.g., by covalent bond formation, adsorption, complex formation, electrostatic interactions, etc.) through a specific functional group. A functional group refers to the reactive part of a molecule, including but not limited to hydroxyl, amino, alkynyl, thiol, nitril, carboxyl, carbonyl, azide, etc.

Alternatively, a synthetic neoepitope peptide corresponding to the identified neoepitope may be synthesized via liquid phase synthesis (see, U.S. Pat. No. 5,516,891), or from smaller peptide fragments. Liquid phase peptide synthesis may be preferred in instances where large-scale production of a particular peptide is needed. In still other embodiments, smaller peptide fragments may be individually synthesized and coupled together to form the desired synthetic peptide sequence. For example, multiple synthetic neoepitope peptides could be synthesized separately, with or without a linker, and then coupled together to form a longer chain.

In other embodiments, synthetic neoepitope peptides could also be produced by expression of a recombinant nucleic acid in a suitable host (e.g., suitable expression systems include viral, bacterial and yeast expression systems). This approach would also be useful in cases where multiple identified neoepitopes are to be on a single amino acid chain, optionally with spacers or cleavage sites (e.g., for proteases) separating the neoepitopes.

Synthetic neoepitope peptides may be synthesized according to other known techniques, including enzymatic synthesis. In enzymatic synthesis, biological enzymes are utilized to form chains of amino acids. Proteases are commonly used due to their stability and selectivity. Proteases not only catalyze the cleavage of peptide bonds but also their formation, as well as hydrolysis of esters and kinetic resolution of racemic mixtures (see, Guzman et al., *Elec J. of Biotech* (2007) 10(2): 1-32).

In some embodiments, the structure of the synthetic neoepitope peptides corresponding to or comprising the identified neoepitope sequences may be $X-L_1-(A_n-L_2)_m-Q$, in which X is an optional coupling group, functional group or moiety that is suitable to covalently or non-covalently attach the synthetic peptide to a solid phase, $L_1$ is an optional linker that covalently links the synthetic peptide to a solid phase or the coupling group. $A_n$ is the synthetic neoepitope peptide having the in silico identified neoepitope sequence with A being a natural (proteinogenic) amino acid and n being an integer between 5 and 50, and most typically between 7 and 11 or 15 and 25. $L_2$ is an optional linker that may be present, especially where multiple synthetic peptide sequences (identical or different) are in the construct, and m is an integer, typically between 1 and 30, and most typically between 2 and 15. Finally, Q is a terminal group which may be used to couple the end of the synthetic peptide to the solid phase (e.g., to sterically constrain the peptide) or to a reporter group (e.g., fluorescence marker) or to another functional moiety (e.g., affinity marker).

Consequently, it should be noted that where the synthetic peptide is used for direct MHC I binding, the overall length will typically be between about 7 and 11 amino acids, 8 and 10 amino acids, and preferably 9 amino acids. Similarly, where the synthetic peptide is used for direct MHC class II binding, the overall length will typically be between about 14 and 20 amino acids or 15-25 amino acids. In principal, once a suitable neoepitope is identified, both MHC class II and MHC class I pathways can be targeted in order to eliminate the tumor from the patient. Longer peptides may be desirable, for example, where the mutated amino acid is not located central to the peptide.

In other embodiments, when the synthetic neoepitope peptide is processed in the cell (typically via proteasome processing) prior to MHC presentation, the overall length will typically be between about 10 and 40 amino acids or longer, with the neoepitope ($A_n$) at or near a central position relative to the length of the synthetic peptide.

For example, X could be a non-covalent affinity moiety (e.g., biotin) that binds a corresponding binding agent (e.g., avidin) on the solid phase, or a functional group (with or without spacer) that reacts with the N- or C-terminal amino or carboxyl group of the synthetic peptide, or a selectively reactive group (e.g., an iodoacetyl or a maleimide group) that reacts with a sulfhydryl group in the synthetic peptide or linker $L_1$. $L_1$ may be used to increase the distance of the synthetic peptide from the solid phase and will therefore typically comprise a flexible linear moiety (e.g., comprising glycol groups, alkoxy groups, glycine, etc.) having a length equivalent to between about 2-20 carbon-carbon bonds (e.g., between 0.3 nm and 3 nm). Of course, it should also be appreciated that the synthetic peptide may use the solid phase on which the peptide was produced and as such may not require a separate coupling group or linker.

Depending on the particular synthetic peptide and coupling method, it should be appreciated that the nature of the solid phase may vary considerably, and all known solid phases and accompanying synthetic processes and chemistries for attachment of peptides are deemed suitable for use herein. For example, suitable solid phases include beads (e.g., agarose beads, polymer beads (color coded or otherwise individually addressable), magnetic beads), surfaces (e.g., wall surfaces of a well in a microtiter plate), paper, nitrocellulose, glass, plastic, metal, composite, or any combination thereof.

The person of ordinary skill in the art will be readily apprised of a suitable choice of solid phase and attachment chemistry. In further preferred aspects, it is also noted that the solid phase will generally be suitable for protocols associated with phage display methods such as allowing molecules presented on a phage (or other scaffold carrier) to reversibly bind to the solid phase (or a synthetic peptide attached to the solid phase) via the molecule presented on the phage. In still further contemplated uses, it should also be recognized that the solid phase may be a carrier protein used in vaccination (e.g., albumin, KLH, tetanus toxoid, diphtheria toxin, etc.), particularly where the synthetic protein is used as a vaccine in a mammal or as an immunogenic compound in a non-human mammal for antibody production. Likewise, the synthetic protein may also be used as a vaccine or immunogenic compound without any carrier. For example, in some embodiments, the synthetic peptide may be injected into the patient, wherein the patient's immune system will treat the synthetic peptide as a foreign antigen to undergo processing by the MHC class II pathway.

In some embodiments, the synthetic neoepitope peptide comprises additional amino acids, attached to the N- or C-terminus, which function to increase binding of the synthetic neoepitope peptide to the cellular component in the bodily fluid. In other embodiments, the synthetic neoepitope peptide comprises additional amino acids to bind to a second epitope on the cellular component.

In still further preferred methods, it should be recognized that where the synthetic peptide (that comprises or corresponds to the cancer neoepitope) is immobilized on a solid phase, affinity agents, and particularly antibodies, to the synthetic neoepitope peptide may be isolated and/or refined. Most preferably, such isolation will include a prefabricated high-diversity library of antibodies.

Synthetic Antibodies

Synthetic antibodies may be generated that immunospecifically bind to synthetic neoepitope peptides. In preferred embodiments, antibody fragments (e.g., scFvs) are screened for binding to a particular synthetic neoepitope peptide, which may be attached to a bead or a surface. Affinity maturation may be employed to improve the affinity of an scFv for a synthetic neoepitope peptide. Once an antibody fragment is identified as suitable for binding to a particular synthetic peptide, the CDRs of this antibody fragment may be grafted into a human or humanized antibody scaffold or backbone, e.g., to form a full length antibody. The full-length antibody may be used for assay validation purposes or for administration as a therapeutic treatment. Therapeutic antibodies that are administered to a patient include full length antibodies as well as antibody fragments (e.g., scFvs, etc.) and are usually human or humanized.

As referred to herein, antibodies include full length antibodies and antibody fragments. The basic full length antibody structure comprises a tetramer that is composed of two polypeptide "light" chains each about 25 kDa and two polypeptide "heavy" chains of about 50 kDa. Light chains may be classified as kappa and lambda, while heavy chains may be classified as mu, delta, gamma, alpha or epsilon, with the heavy chain determining the antibody's isotype (e.g., IgA, IgD, IgE, IgG, IgM).

Each chain comprises a variable region of about 100 to 110 (or more) amino acids that govern epitope (or, in this case, synthetic neoepitope peptide) recognition, and the variable regions of each light and heavy chain together form the antibody binding site. The carboxy-terminal portion of each chain includes a constant region Fc, primarily involved in effector function.

The heavy chains and light chains have a general structure of relatively conserved framework regions (FR) joined by three hyper variable regions or CDRs (CDR1, CDR2, CDR3). The CDRs from the heavy and the light chains, which are aligned by the framework regions, enable binding to a specific synthetic neoepitope peptide.

Antibodies may be of any origin including but not limited to human, murine (e.g., mouse and rat), donkey, rabbit, goat, guinea pig, bird, camel, horse, or chicken. For therapeutic purposes, antibodies that are human or that have been humanized are preferred.

Synthetic neoepitope peptide-binding antibody fragments, including single-chain antibodies, may comprise the variable region(s) alone or in combination with the entirety or a portion of antibody hinge regions or constant regions.

The antibodies as described herein may be monospecific, bispecific, trispecific or of higher multispecificity. Multispecific antibodies may be specific for different epitopes, e.g., two or more synthetic neoepitope peptides. Here, it is presumed that the multispecific antibody only binds to neoepitopes and not to other off target molecules.

Human or humanized antibodies are particularly desirable for therapeutic treatment of human patients. Human or humanized antibodies can be made by a variety of methods known in the art including phage display or mRNA display as described herein, e.g., using antibody libraries derived from human immunoglobulin sequences.

Any methodology known in the art for screening large combinatorial libraries to identify antibodies that bind synthetic neoepitope peptides can be applied, including but not limited to phage display, yeast surface display, ribosome display, or mRNA display, or any combination thereof (see, Harlow et al., Antibodies: A Laboratory Manual, Cold Spring Harbor Laboratory Press, 2nd ed. 1988; Hammerling et al., Monoclonal Antibodies and T-Cell Hybridomas (1981) 563-681; WO 98/31700). Antibodies (including antibody fragments or variants thereof) can be produced by any method known in the art. For example, scFv libraries can be generated and used in conjunction with phage display or mRNA display technology can be used to identify antibody fragments that bind to synthetic neoepitope peptides as is exemplarily described in WO 2016/172722. Additionally, antibodies may be chemically synthesized or produced through the use of recombinant expression systems. Two methods for screening large combinatorial libraries are described as follows.

Phage Display

In phage display methods, functional antibody domains are displayed on the surface of phage particles, which carry the polynucleotide sequences encoding the antibody domains. In a particular embodiment, such phage can be utilized to display antigen binding domains expressed from a repertoire or combinatorial antibody library (e.g., human or murine scFv library). Phage expressing an antigen binding domain that binds the antigen, in this case the synthetic neoepitope peptide, can be selected or identified, e.g., using synthetic neoepitope peptides that are bound or captured to a solid surface or bead.

Phage display may also be used for in vitro affinity maturation of an antibody that binds to a synthetic neoepitope peptide. For example, the CDR regions of the VH and VL domains, in particular, may be mutated in vitro, e.g., using error-prone PCR and/or gene shuffling. Expression of VH and VL domains with "mutant" CDRs in a phage display library allows for the selection of VH/VL combinations that bind to a given synthetic neoepitope peptide with preferred binding characteristics such as improved affinity or improved off rates.

In a typical method, a high-diversity library may be a phage display library having a diversity of at least $10^9$ diverse members, or at least $10^{10}$ diverse members, or even higher, typically based on M13 or fd phages and display via pIII, pVIII, pVI, pVII, or pIX, or based on T7 phages and the gene 10 capsid protein. Binding domains typically include Fab, Fv, scFv, or disulfide stabilized Fv antibody domains. As should be readily appreciated, use of large diversity libraries will provide in relatively short time several binding candidate antibodies that can be further selected for best binders. Indeed, where binding affinity to the immobilized synthetic peptide is less than desired, it should be recognized that affinity can be improved via affinity maturation using protocols well known in the art. For example, low affinity ($K_D>10^{-7}$M) binders or members of smaller libraries may be subjected to affinity maturation to improve binding affinity and/or kinetics using methods well known in the art (see e.g., Carmen S., et al., Briefings In Functional Genomics And Proteomics. Vol 1. No 2. 189-203. July 2002). In addition, it should be noted that while antibody libraries are generally preferred, other scaffolds are also deemed suitable and include beta barrels, ribosome display, cell surface display, etc. (see e.g., Hosse R., Protein Sci. (2006) January; 15(1): 14-27.) Thus, it should be appreciated that in preferred aspects the synthetic peptide is used as a bait (epitope) in a library of antibodies to identify high-affinity binding ($K_D<10^{-7}$M, and more typically $K_D<10^{-8}$M) antibodies.

Examples of phage display methods that can be used to make the antibodies describd herein include those disclosed in Brinkman et al., J. Immunol. Methods 182:41-50 (1995); WO 90/02809; and U.S. Pat. No. 5,969,108.

mRNA Display

As an alternative to phage display, mRNA display may be used to obtain antibodies that bind to the synthetic neoepitope peptide. In some embodiments, the synthetic antibody is generated based upon a mRNA display method (see, recombinant antibody library expressed as RNA-protein fusions, as described in WO 98/31700 (Szostak and Roberts); and also Roberts and Szostak, Proc. Nat'l Acad. Sci. USA, 94:12297-12302 (1997)). In an mRNA display method, a covalent bond is formed between a synthetic mRNA and the corresponding peptide (e.g., an antibody, antibody domain, etc.) that it encodes. In particular, during in vitro translation of a synthetic mRNA carrying puromycin (a peptidyl acceptor antibiotic) at its 3' end, the puromycin forms a covalent linkage with the expressed peptide.

This technology allows a specific mRNA to be enriched from a mixture of mRNAs (e.g., a combinatorial library) based on the properties of the encoded antibody or fragment thereof. Thus, antibodies or fragments thereof that bind to an antigen (e.g., a synthetic neoepitope peptide) can be identified and isolated.

In one embodiment, mRNA display is used for in vitro evolution of scFv antibody fragments. Here, a random scFv library may be constructed, e.g., using error prone PCR and/or DNA shuffling, random mutagenesis or other techniques to modify genes encoding scFvs. The scFv library is transcribed, and the resultant mRNA is enzymatically ligated to puromycin. The scFv library is then transcribed in vitro, and the resultant expressed scFv is ligated to puromycin. In some embodiments, the synthetic neoepitope peptide is ligated to a bead or other surface. The mRNA/antibody fragment complexes are brought into contact with the synthetic peptide under conditions suitable to promote binding, and non binders are washed away. The bound molecules may be eluted by protease digestion or other suitable means of obtaining the mRNA. The mRNA is then reverse transcribed into cDNA for cloning, amplification and sequencing (see, Fukuda, *Nucleic Acids Res.* (2006) 34(19): 1-8). mRNA display for selection of antibodies from large repertoires is also described in, e.g., Brekke & Sandlie, *Nat. Rev. Drug Discovery* (2003) 2:52-62 and U.S. Pat. No. 8,623,358.

Additionally, these nucleic acid sequences can be subjected to further affinity maturation by additional rounds of screening of mRNA-peptide fusions in which mutations have been introduced into the originally selected sequence(s), or by other in vitro methods for affinity maturation of recombinant antibodies.

Depending upon how the peptide/mRNA complex is processed, the synthetic neoepitope peptide, the synthetic neoepitope peptide plus RNA, or the synthetic neoepitope peptide plus a tag may be recovered.

Nucleic acid sequences encoding antibodies or fragments thereof recovered from screening of combinatorial libraries for specificity to a given synthetic neoepitope peptide can be expressed by recombinant means (e.g., in mammalian host cells).

Grafting

For phage display or mRNA display, as the antibodies are directly coupled to the cell that carries the nucleic acid(s) encoding these antibodies, it should be further appreciated that such nucleic acid(s) can then be analyzed to identify sequence elements encoding the hypervariable loops (CDR1, CDR2, and CDR3), for light and heavy chains, respectively, and/or specificity determining residues (SDRs). Most typically, determination of residues is performed using standard sequencing methods.

Once determined, it is then contemplated that the hypervariable loops, or the CDR1-H, CDR2-H, and/or CDR3-H and/or the CDR1-L, CDR2-L, and/or CDR3-L, and/or SDRs are grafted onto a human or humanized antibody scaffold or antibody (see, U.S. Pat. No. 5,225,539). As will be readily appreciated, grafting can be done by genetic engineering of a nucleic acid that encodes a human or humanized antibody scaffold or antibody. For example, within each CDR, there are variable positions that are directly involved in the interaction with antigen, i.e., specificity-determining residues (SDRs), and there are conserved residues that maintain the conformations of CDRs loops. SDRs may be identified from the 3D structure of the antigen-antibody complex and/or the mutational analysis of the CDRs or other means. For example, a SDR-grafted humanized antibody can be constructed by grafting the SDRs and the residues maintaining the conformations of the CDRs onto a human template. Consequently, it should be recognized that human or humanized antibodies with specificity to cancer neoepitopes can be prepared in an entirely synthetic manner in which the antibody is expressed in a cell that has not previously contacted the antigen. Grafting the CDR regions of antibodies (e.g., the CDR regions that bind to the synthetic neoepitope peptides obtained by phage display, mRNA display, etc.) to a human or humanized antibody scaffold or antibody allows rapid generation of antibodies to treat a human disease. Other methods of producing antibodies, e.g., mammalian immune system, can take 3-4 months to produce an antibody and is a slow and costly process. Thus, in some embodiments, antibodies embodiments may be prepared without the use of a mammalian immune system. Moreover, contemplated methods allow production of patient and cancer specific antibodies for treatment of a patient that has failed to produce or effectively use other antibodies, such as antibodies produced by the patient's own immune system or commercially produced therapeutic antibodies against the cancer neoepitopes. Once the CDRs are grafted onto a human or humanized antibody scaffold using recombinant DNA techniques, the modified gene can be recombinantly expressed to produce an antibody that specifically binds to the neoepitope displayed on the surface of the tumorigenic cell.

Prepared synthetic antibodies can be used directly as an IgG (or other isotype), as a fragment (e.g., bispecific Fab or other bispecific fragment), and/or as a chimeric protein (e.g., scFv as ectodomain in a chimeric T cell receptor), alone or in combination with a therapeutic or diagnostic agent (including cases in which the agent is conjugated to the antibody), and/or as a hybrid protein with a transmembrane domain to ensure membrane anchoring of the antibody to a cell. Consequently, a method of generating a pharmaceutical agent or composition for cancer immune therapy is contemplated in which the synthetic antibodies are coupled to a therapeutic or diagnostic agent (which may have a cellular or non-cellular component) to obtain the pharmaceutical agent or composition.

Tumor Cell Enrichment or Isolation for Validation

Once synthetic antibodies have been generated by mRNA display, phage display, or other techniques, the synthetic antibodies may be used to detect tumor cells to validate display of neoepitopes, or enrich tumor cells (e.g., circulating tumor cells (CTCs), metastatic cells, circulating microvesicles, circulating exosomes, circulating membrane fragments, etc.) present in the patient for additional studies.

In order to perform the validation or enrichment, a bodily fluid comprising a cellular component is obtained from a patient. Bodily fluids include but are not limited to blood, serum, plasma, saliva, urine, tear, sweat, interstitial fluid, lymph fluid, cerebrospinal fluid, mucosa secretion, peritoneal fluid, or other bodily secretions or exudates. In some embodiments, the bodily fluid undergoes additional processing, before being brought into contact with the synthetic antibody. Such processing may include steps to remove white blood cells from the sample, including lysing of erythrocytes, removal of erythrocytes, and/or removal of the buffy coat. It is estimated that about one CTC is present in a blood sample for every billion normal or blood cells. By targeting neoepitopes, CTCs expressing these sequences can be specifically detected and isolated.

The cellular component may be a circulating tumor cell, a metastatic cell, a circulating microvesicle, an exosome, or a circulating membrane fragment, etc. In general, the cellular component comprises a cell or membranous material displaying the neoepitope on its surface.

Circulating tumor cells (CTCs) are cells that detach from a primary tumor and travel through the bloodstream or lymphatic system to other parts of the body. By isolating CTCs and bringing these cells into contact with synthetic antibodies, it can be determined whether in silico identified neoepitopes are present on the surface of the tumorigenic cell. If the identified neoepitope is displayed on the surface of the tumor cell, the synthetic antibody will bind to the displayed neoepitope. This effectively validates the in silico identified neoepitope as a therapeutic target for personalized cancer therapy. Otherwise, if the synthetic antibody does not bind to the cell surface, a different in silico identified neoepitope should be selected, and the validation process (e.g., synthesis of a neoepitope peptide, generation of a synthetic antibody, detection of the neoepitope on the cell surface) repeated.

Other types of cells and cellular components can be assayed for the presence of neoepitopes. For example, metastatic cells are cells that may also enter the bloodstream or lymphatic system while in the process of invading other tissues. These types of cells can also display neoepitopes. Microvesicles, which are fragments of plasma membrane, may also be shed from cells displaying the neoepitope, and therefore, may also display the neoepitope on their surface. These types of cells and/or components may also be contacted with the synthetic antibody to test for the presence of a neoepitope.

In some embodiments, the cellular component comprises exosomes, which contain cellular material from their cell of origin. Thus, an exosome originating from a tumorigenic or cancerous cell can comprise one or more of DNA, RNA, proteins, lipids, and metabolites, including neoepitopes from the tumorigenic or cancerous cells. Exosomes can also transfer molecules from one cell to another via membrane vesicle trafficking, thereby influencing the immune system, e.g., dendritic cells and B cells, and may play a functional role in mediating adaptive immune responses to pathogens and tumors. Exosomes may also be contacted with a synthetic antibody to test for the presence of a neoepitope.

Thus, the cellular component may be brought into contact with a synthetic antibody that specifically binds to the neoepitope(s). According to certain embodiments, the synthetic antibody can comprise a detectable moiety. In some embodiments, the detectable moiety may be a radionuclide (e.g., $^{11}C$, $^{13}N$, $^{15}O$, $^{18}F$, $^{123}I$, $^{99m}Tc$, $^{133}Xe$, $^{201}Tl$, $^{18}F$, etc.) detectable by radiometric techniques (e.g., PET, SPECT, beta radiation, gamma radiation, other radiation based techniques, etc.). In other embodiments, the detectable moiety may be optically and quantitatively detectable (e.g., colorimetric assays such as ELISA, immunohistochemistry, etc.).

Any detectable means may be used to detect binding of the synthetic antibodies to the neoepitopes displayed on the surface of the cells. In some embodiments, the synthetic antibody is labeled with a colorimetric probe, a fluorescent tag, a chemiluminescent tag, or a radiolabel, and incubated with the bodily fluid comprising cells or cellular components. A variety of techniques are suitable for detecting binding of an antibody to a cellular component (https://www.rndsystems.com/resources/protocols/detection-visualization-antibody-binding). Such techniques, including various fluorescently tagged, colorimetric, chemiluminescent, or radiolabeling immunoassays, are well known to a skilled artisan.

In some embodiments, the tumor cells may be placed on tissue culture plates or other surfaces coated with materials that enhance binding, e.g., poly-lysine coatings, gelatin, collagen, fibronectin, laminin, etc. After incubation of the tumorigenic cells with the labeled synthetic antibody, excess unbound synthetic antibody can be removed using a wash step. The remaining adhered cells can undergo imaging or other colorimetric analysis to determine whether the synthetic antibody is bound to the surface of the tumor cells.

In other embodiments, membrane fragments may be fixed to a surface and then incubated with the labeled synthetic antibody. After incubation of the membrane fragment with the labeled synthetic antibody, excess unbound synthetic antibody can be removed using a wash step. The membrane fragments can undergo imaging or other colorimetric analysis to determine whether the synthetic antibody is bound to the membrane surface. Many other techniques for visualizing antibodies binding to cell surface receptors are known in the art, and all such methods are contemplated.

In other embodiments, it may be desirable to isolate or enrich the CTC cells. In some embodiments, the synthetic antibodies are coupled to a surface and the tumor cells are brought into contact with the synthetic antibodies. In this example, the surface is generally non-adherent to cells. When the synthetic antibody binds to the neoepitope displayed on the surface of a tumor cell, e.g., a CTC cell, the cell population expressing the neoepitope can be enriched, and other cells and contaminants can be washed away. Labeled synthetic antibody can then be added to detect the presence of the neoepitope.

In other embodiments, cells may be isolated using commercially available kits (e.g., https://tools.thermofisher.com/content/sfs/manuals/dynabeads_flowcotmplexi_buffvwb-_man.pdf by Thermo Scientific). For example, cell isolation kits compatible with custom antibodies, e.g., the synthetic antibodies described herein, can be used to isolate cells. In this example, the synthetic antibodies may be labeled with DSB-X biotin, and incubated with tumorigenic cells that express the neoepitope. Magnetic beads (Dynabeads) are added that bind to the labeled antibody. A magnet may be used to separate cells that are bound to the magnetic beads, and those that are not bound to the magnetic beads (lacking expression of neoepitope) may be washed away. The beads may be released from the cells, and isolated tumor cells displaying the neoepitope may be obtained.

In other embodiments, antibodies are coupled to a fluorescent dye, allowing specific cells expressing the neoepitope to be labeled. The labeled cells can then be separated using a fluorescence activated cell sorter (FACS). In some embodiments, the synthetic antibody is contacted with bodily fluid in the FACS (or prior to injection into the FACS).

In still other embodiments, microfluidic devices may be used to enrich tumor cells displaying neoepitopes. In many cases, tumor cells are larger than blood cells, e.g., tumor cells may range in size from 10-20 µm in diameter while blood cells may range from 7-12 µm in diameter. Microchips can be designed to separate cells based on size, allowing for enrichment of tumor cells (Warkiani et al., Lab Chip, (2014) 14:128-137; Ozkumur et al., Sci Transl Med (2013) 5:179ra47). In some embodiments, the synthetic antibody is contacted with bodily fluid in the microfluidics device (or prior to injection into the microfluidics device).

In all of the above noted embodiments, it should be appreciated that where the biological fluid is whole blood, the whole blood may be debulked to enrich the blood sample in circulating tumor cells or other membranous vesicles. While debulking can be performed in numerous manners known in the art, it is particularly preferred that debulking includes removal of red and white blood cells via antibody-mediated removal and centrifugation as is described in U.S. Pat. No. 8,569,009.

Many other techniques for isolating cells using labeled antibodies are known in the art and all such methods are contemplated. Various protocols exist for isolating cells using antibodies, all of which are contemplated for use herein.

Therapeutic Approaches and Validation

A consequence of the cell enrichment or isolation techniques presented herein is that validation is provided regarding display of certain neoepitopes on the surface of the tumorigenic cell. Thus, it should be appreciated that efficacy of any treatment that targets one or more neoantigens/neoepitopes on a tumor cells can be predicted by correlating the presence of the neoantigens/neoepitopes on the cell (and with that the 'visibility of the neoantigen/neoepitope to the immune system) with likely therapeutic effect of the treatment and/or by experimental in vitro validation of an immune response to the presented neoantigen/neoepitope. For example, a method of ex vivo validating immune therapy that targets a neoepitope of a tumor of a patient is contemplated where the neoantigen/neoepitope is detected using synthetic antibodies contemplated herein. Upon detection, presence of the targeted neoepitope on the tumor can be ascertained. In another example, a method of validating an immune therapy that targets a neoepitope of a tumor is contemplated in which a cellular component (e.g., circulating tumor cell) is exposed in vitro to a modified immune competent cell (e.g., T cell expressing a chimeric antigen receptor with a synthetic antibody portion or NK cell bound to synthetic antibody). An in vitro immune response of the modified immune competent cells against the cellular component is then predictive of likely treatment success. In still another example, a method of validating adjuvant chemotherapy to immune therapy is contemplated in which a synthetic antibody against a tumor- and patient-specific neoepitope is used to enrich or isolate a cellular component, which is then exposed to a chemotherapeutic drug. Cell killing is then indicative of sensitivity of the cellular component to the drug. In still further examples, a method of ex vivo validating immune therapy is contemplated that uses a synthetic antibody to bind to the cellular component. Binding and detection of the antibody is then indicative of the presence of the neoepitope on the tumor. In yet another example, a method of validating immune therapy is contemplated that uses a synthetic antibody to enrich or isolate a cellular component, which is then exposed to immune competent cells of the patient (possibly using immune stimulatory cytokines), which will be predictive of an immune response of the patient to the neoepitope or neoantigen.

Antibodies, antibodies conjugated to (or in addition to) chemotherapeutic drugs, antibodies conjugated to radionuclides (e.g., a radioisotope, a PET detectable isotope, a SPECT detectable isotope, etc.), or to any other molecular compound that is capable of specifically binding to the neoepitope can be administered to the patient for killing the tumorigenic cell and/or for detection of the tumorigenic cell. In other embodiments, antibodies may be administered along with checkpoint modulators in order to unleash an immune system response to recognize and destroy tumorigenic or cancerous cells. In still other embodiments, antibodies may be administered along with immune competent cells and/or modified immune competent cells in order to unleash an immune system response to recognize and destroy tumorigenic or cancerous cells.

Once enriched or isolated, the tumor cells can be propagated in cell culture according to techniques known in the art. These propagated cells can be used to validate chemotherapeutic drugs, validate high affinity NKs (haNKs), target activated NKs (taNKs), activated NK (aNKs), NK92 cells (e.g., commercially available from Nantkwest, 9920 Jefferson Blvd. Culver City, Calif. 90232), can train the patient immune system on cancerous or tumorigenic cells (e.g., using ADCC processes, CAR T-cells, vaccines derived from neoepitopes, checkpoint inhibitors, etc.), or can be used to further validate that the tumorigenic cells of the patient express other in silico identified neoepitopes.

Radiologic agents may also be coupled to the antibody administered to a patient to selectively destroy a cancer cell. Suitable radiologic agents include $^{125}$I, $^{131}$I, $^{90}$Y, $^{177}$Lu, or $^{192}$Ir. Likewise, imaging agents may be coupled to the antibody or fragment thereof, and especially preferred imaging agents include PET (e.g., $^{11}$C, $^{13}$N, $^{15}$O, and $^{18}$F) and SPECT labels (e.g., $^{123}$I, $^{99m}$Tc, $^{133}$Xe, $^{201}$Tl, and $^{18}$F).

Immune Competent Cells

In some embodiments, antibodies, e.g., full-length IgG antibodies, specific to the neoepitope can be generated and administered to the patient. For example, the CDRs of the scFv determined to bind to the neoepitope (based on phage display or mRNA display) can be grafted into a human or humanized IgG backbone. The full length IgG, specific for the neoepitope, may be mixed with the bodily fluid. IgG antibodies are involved in triggering ADCC responses, which lead to lysis and destruction of the tumor cell. ADCC is often mediated by NK cells, but other immune competent cells including macrophages, neutrophils and eosinophils may also mediate this process. Thus, in some embodiments, the CDRs of the synthetic antibody may be grafted into an IgG backbone or scaffold and administered to the patient in order to trigger an ADCC response for tumor cells displaying the neoepitope. In other embodiments, the CDRs of the synthetic antibody may be grafted into an IgG backbone or scaffold and administered to the patient in order to trigger an antibody dependent cellular phagocytosis (ADCP) response, a process in which macrophages attack and destroy cells, for tumor cells displaying the neoepitope In one embodiment, a bodily fluid is obtained, wherein the bodily fluid comprises cellular components, e.g., tumorigenic cells displaying the neoepitope. The synthetic antibody is contacted with the cellular components under conditions to promote binding of the synthetic antibody to the displayed neoepitope. Immune competent cells are contacted with the synthetic antibody bound to the neoepitope on the tumor cell surface. Assays are then performed to detect immune responses, e.g., indicating that an ADCC response or an ADCP response has been triggered by the patient's own immune cells.

While it is generally contemplated that all cytotoxic cells are deemed suitable for use herein, especially preferred cytotoxic cells include CD8+ T cells and NK cells (even if of different origin). However, it should be appreciated that in other embodiments, the cytotoxic cell or immune competent cell may also be, e.g., a macrophage, a dendritic cell, a monocyte, a neutrophil cell, a basophile, or eosinophil cell. Therefore, and viewed from a different perspective, the immune competent cells contemplated herein may effect their cytotoxic action via phagocytosis, pore formation, induction of antibody-dependent cell-mediated cytotoxicity (ADCC), by triggering TNF or fas mediated killing pathways, etc. Thus, according to certain embodiments, immune competent cells may be brought into contact with the bodily fluid and with the antibodies as described herein. In particular embodiments, the immune competent cells, e.g., cytotoxic CD8+ cells or NK cells, target tumorigenic cells for destruction.

Assays for detecting an immune response are known in the art and are described herein. For example, assays for detecting such a response may detect a release of cytotoxic granules (e.g., granulysin, perforin, granzymes), or phagocytosis, or receptor-ligand mediated cytolysis (e.g., as mediated by the Fas/APO pathway). A variety of flow cytometric assays are available for monitoring cell-mediated cytotoxicity, e.g., based on presence of lytic granules such as perforin, granzymes, or production of TNF family members, e.g., TNF-α, FasL or TRAIL (Zaritskaya 2010, Clay, T. et al., Clin. Cancer Res. (2001) &:1127-1135).

In other embodiments, immune stimulatory cytokines are added to promote or trigger an immune response. Cytokines include but are not limited to IL2, IL4, IL7, IL11, IL15, IL21, TFN-alpha, IFN-gamma, etc. In some embodiments, cytokines can reactivate exhausted T cells, which is a state of dysfunction in T cells in which the T cells are not able to respond to effector function and have an altered transcriptional state.

Moreover, it is contemplated that the cytotoxic or immune competent cells may be an autologous cell (that may be appropriately genetically engineered to display a chimeric antigen receptor (CAR) or may be an otherwise modified chimeric protein capable of recognizing the neoepitope of the tumorigenic cell), or a heterologous cell that may be a primary cell or a cell derived from a cell culture. Cytotoxic T cells can be genetically engineered to express a CAR specific to the neoepitope. For example, techniques are known in the art for grafting the specificity of an antibody (e.g., a monoclonal antibody, a scFv, etc.) to an antigen receptor in the T cell, e.g., using retroviral vectors. These modified CAR T cells can be reintroduced into the patient to recognize and eliminate the tumorigenic cell. Immune response assays can be performed to validate whether or not the CAR T cell has activity against the tumorigenic cell.

Regardless of the source of the cell, it is generally contemplated that the cell is a mammalian cell, and especially a human cell. Additionally, and particularly where the cells are not obtained from the mammal that is to receive the subsequently modified cells, it is contemplated that the cells are rendered less immunogenic to the mammal (e.g., via HLA grafting or deletion of MHC complexes). Of course, it should also be appreciated that multiple different cell populations may be prepared that have different combinations or sub-combinations of Fc receptors and signaling moieties to even further increase the anticipated therapeutic effect. For example, two different populations of NK cells may be administered where the first type of Fc receptor is CD16a and where the cell overexpresses Fc γ-signaling subunits, and where the second type of Fc receptor is CD32a and where the cell overexpresses Fc γ-signaling subunits. In another example, two different populations of cells may be administered where the first cell is an NK cell expressing CD16a and overexpressing Fc γ-signaling subunits, and where the second cell is a CD8+ T-cell expressing CD16a and overexpressing Fc γ-signaling subunits.

In yet another example, suitable NK cells for administration may be (or may be derived from) previously established therapeutic cell lines, which are well known in the art. For example, suitable cell lines include aNK cells, haNK cells, taNK cells, NK92 cells (e.g., commercially available from Nantkwest, 9920 Jefferson Blvd. Culver City, Calif. 90232) or TALL 104 cells (e.g., commercially available from ATCC, CRL-11386, 10801 University Boulevard, Manassas, Va. 20110 USA).

Checkpoint Modulators

Immune checkpoint modulators help regulate pathways of the immune system that are involved in self-tolerance as well as control the amplitude and duration of immune responses. In some embodiments, a tumor cell may express (or overexpress) a checkpoint modulator that inhibits a cytotoxic T cell response against the tumor cell. Accordingly, in some cases, it may be desirable to administer a molecule which alleviates checkpoint inhibition (alleviates a negative regulatory element) in order to overcome checkpoint inhibition to facilitate or augment a host immune attack against the tumorigenic or cancerous cell. In other embodiments, it may be desirable to administer a molecule which positively regulates checkpoint inhibition (promotes a positive regulatory element) in order to stimulate or enhance signaling of positive regulators of immune responses in order to facilitate or augment a host immune attack against the tumorigenic or cancerous cell. Examples of checkpoint mechanisms which may be targeted include those that involve signaling though at least one of CTLA-4, PD-1, PD-L1, GITR, OX40, LAG-3, KIR, TIM-3, CD28, CD40 and CD137.

In some embodiments, immune checkpoint modulators or compositions thereof are administered in a therapeutically effective amount. Immune checkpoint modulators include but are not limited to, e.g., CTLA-4 blockers such as ipilumimab or tremelimumab, and/or other agents. Checkpoint inhibitors that have been approved by the FDA include Pembrolizumab (Keytruda), Nivolumab (Opdivo), Atezolizumab (Tecentriq), Avelumab (Bavencio), and Ipilimumab (Yervoy).

In some embodiments, an immune checkpoint modulator is administered with an antibody having specificity for a neoepitope displayed on a cancer cell. In other embodiments, an immune checkpoint modulator is administered in conjunction with an antibody having specificity for a neoepitope displayed on a cancer cell and immune competent cells.

Chemotherapy

Contemplated herein are chemotherapeutic drugs which may be administered in combination with the antibodies described supra. Also contemplated herein are chemotherapeutic agents which may be administered in combination with antibodies and immune competent cells and optionally checkpoint inhibitors. Various assays for determining in vitro sensitivity to chemotherapeutic agents are known in the art (see, Udelnow, *Prezegl Chir* (2013), 85(6):340-7). In some embodiments, pathway modeling analysis software, e.g., PARADIGM, may be utilized to select a particular chemotherapeutic drug to target a particular pathway.

In some embodiments, the antibodies may be conjugated to the chemotherapeutic drug, in order to deliver the chemotherapeutic drug directly to a cancer cell. In other embodiments, the antibodies may be delivered separately than the chemotherapeutic drug, as combination therapy. Suitable chemotherapeutic drugs include kinase inhibitors (e.g., erlotinib, imatinib, bortezomib, etc.), topoisomerase inhibitors (e.g., topotecan, etoposide, teniposide, etc.), nucleotide analogs (e.g., fluorouracil, gemcitabine, azacytidine, etc.), platinum based agents (e.g., cisplatin, carboplatin, etc.), alkylating agents (e.g., cyclophosphamide, chlorambucil, temozolomide, etc.), taxanes (e.g., docetaxel, paclitaxel, etc.), microtubulin inhibitors (e.g., vincristine, vinblastine, etc.), antimetabolites, cytotoxic drugs, cell cycle inhibitors, or DNA repair inhibitors.

Techniques to treat cancer include surgery, radiation therapy, chemotherapy, immunotherapy, targeted therapy, hormone therapy, stem cell transplant, or other precision methods. Any of these techniques may be combined with embodiments as described herein to treat cancer.

Embodiments that are useful for the identification of neoepitopes associated with tumors or cancers, include, but are not limited to: Acute Lymphoblastic Leukemia (ALL), Acute Myeloid Leukemia (AML), Adrenocortical Carcinoma, AIDS-Related Cancers (including Kaposi Sarcoma, AIDS-Related Lymphoma, Primary CNS Lymphoma), Anal Cancer, Astrocytomas, Basal Cell Carcinoma, Bile Duct Cancer, Bladder Cancer, Bone Cancer, Brain Tumors, Breast Cancer, Bronchial Tumors, Burkitt's Lymphoma, Carcinoid Tumor, Carcinoma, Cardiac Tumors, Central Nervous System Cancers (including Atypical Teratoid/Rhabdoid Tumor, Ependymoma, Embryonal Tumors, Germ Cell Tumors), Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma, Ductal Carcinoma In Situ (DCIS), Endometrial Cancer, Esophageal Cancer, Esthesioneuroblastoma, Extracranial Germ Cell Tumor, Extragonadal Germ Cell Tumor, Eye Cancer (including Intraocular Melanoma and Retinoblastoma), Fallopian Tube Cancer, Fibrous Histiocytoma, Gallbladder Cancer, Gastric Cancer, Gastrointestinal Carcinoid Tumor, Gastrointestinal Stromal Tumors, Germ Cell Tumors, (including Extragonadal Germ Cell Tumors, Ovarian Germ Cell Tumors, and Testicular Cancer), Gestational Trophoblastic Disease, Hairy Cell Leukemia, Head and Neck Cancer, Hepatocellular Cancer, Hodgkin's Lymphoma, Hypopharyngeal Cancer, Intraocular Melanoma, Islet Cell Tumors, Kaposi's Sarcoma, Kidney Cancer, Langerhans Cell Histiocytosis, Laryngeal Cancer, Leukemia, Lip and Oral Cavity Cancer, Liver Cancer, Lung Cancer, Lymphoma, Malignant Fibrous Histiocytoma, Melanoma, Merkel Cell Carcinoma, Mesothelioma, Metastatic Cancer, Metastatic Squamous Neck Cancer, Multiple Myeloma, Mycosis Fungoides, Myelodysplastic Syndromes, Myelodysplastic Neoplasms, Myelogenous Leukemia, Myeloid Leukemia, Myeloproliferative Neoplasms, Chronic Nasal Cavity and Paranasal Sinus Cancer, Nasopharyngeal Cancer, Neuroblastoma, Non-Hodgkin Lymphoma, Non-Small Cell Lung Cancer, Oral Cancer, Lip and Oral Cavity Cancer, Oropharyngeal Cancer, Osteosarcoma and Malignant Fibrous Histiocytoma of Bone, Ovarian Cancer, Pancreatic Cancer, Pancreatic Neuroendocrine Tumors, Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm, Pleuropulmonary Blastoma, Primary Central Nervous System Lymphoma, Primary Peritoneal Cancer, Prostate Cancer, Rectal Cancer, Renal Cell Cancer, Retinoblastoma, Rhabdomyosarcoma, Salivary Gland Cancer, Sarcoma, Osteosarcoma, Uterine Sarcoma, Sezary Syndrome, Skin Cancer, Small Cell Lung Cancer, Small Intestine Cancer, Soft Tissue Sarcoma, Squamous Cell Carcinoma of the Skin, Squamous Neck Cancer, Stomach Cancer, T-Cell Lymphoma, Testicular Cancer, Throat Cancer, Thymoma and Thymic Carcinoma, Thyroid Cancer, Ureter and Renal Pelvis Cancer, Urethral Cancer, Uterine Cancer, Uterine Sarcoma, Vaginal Cancer, Vascular Tumors, Vulvar Cancer, and Wilms Tumor.

In some embodiments, the nucleotide sequence encoding the neoepitope may be cloned into an expression vector, and the expression vector introduced into a host cell using any suitable technique known in the art, e.g., transfusion, injection, transfection, etc. In other embodiments, the nucleotide sequence encoding the neoepitope may be integrated into the chromosome of the host cell. In still other embodiments, the expression system is suitable for recombinant expression in eukaryotic systems. In other embodiments, the expression system is suitable for recombinant expression in mammalian systems. Such techniques are well known in the art, e.g., (Griffiths, et al., recombinant DNA technology in eukaryotes, in An Introduction to Genetic Analysis (2000), New York). The patient cell line expressing the neoepitope can be used for antibody generation, e.g., to be used as a therapeutic agent/immune therapeutic.

Based on the results of ongoing testing with the patient, treatment may be modified. For example, if a patient is receiving a therapeutic treatment to reduce or eliminate the tumor, and the cellular component shows a level of neoepitope corresponding to the presence of the tumor that is about the same or increasing (as compared to the level at initiation of treatment), this would indicate that the therapeutic treatment is not working, and an alternative therapeutic treatment should be selected.

Therapeutic compounds and compositions may be administered to a patient using appropriate formulations, indications, and dosing regimens suitable by government regulatory authorities such as the Food and Drug Administration (FDA) in the United States.

In some embodiments, an antibody having specificity to the neoepitope, a checkpoint inhibitor, a chemotherapeutic or immune competent cells, or any combination thereof are administered to a patient as one or more pharmaceutical compositions. The pharmaceutical composition may include a physiologically acceptable carrier or excipient. Additionally, pharmaceutical compositions may comprise one or more buffers, coloring, flavoring and/or aromatic substances, emulsifiers, lubricants, pH buffering agents, preservatives, salts for influencing osmotic pressure, stabilizers, wetting agents, etc., which do not deleteriously react with the active compounds (e.g., antibodies, checkpoint modulators, chemotherapeutics, etc.) or otherwise interfere with their activity.

Pharmaceutical compositions may be formulated for a particular mode of administration. Modes of administration may include but are not limited to: topical, intravenous, intraperitoneal, subcutaneous, intranasal or intradermal routes. In other embodiments, the composition can be directly administered to a target tissue, such as heart or muscle (e.g., intramuscular), or nervous system (e.g., direct injection into the brain, intraventricularly, intrathecally), parenterally, transdermally, or transmucosally (e.g., orally or nasally).

The pharmaceutical compositions are administered in a therapeutically effective amount, which is the amount effective for treating the specific indication. In general, the pharmaceutical compositions will be administered in an amount of at least about 10 µg/kg body weight and in most cases they will be administered in an amount not in excess of about 8 mg/kg body weight per day. In most cases, the dosage is from about 10 µg/kg to about 1 mg/kg body weight daily, taking into account the routes of administration, symptoms, etc.

In some embodiments, the pharmaceutical composition is formulated for intravenous administration. Such formulations may be prepared according to standard techniques known by one of ordinary skill in the art. For example, a composition that is to be administered intravenously may have one or more ingredients (e.g., an antibody) that is in lyophilized form as a dry lyophilized powder or water free concentrate in a hermetically sealed container. In such cases, the antibody may be mixed with a suspension buffer, with sterile pharmaceutical grade water, saline or dextrose/water, etc. prior to infusion in the patient.

Administration may occur as a one-time dose or based on an interval. As used herein, "interval" indicates that the therapeutically effective amount is administered periodically (as distinguished from a one-time dose). The administration interval for a single individual need not occur at a fixed interval, but can vary over time. The term, "in combination with," or "co-administered" indicates that a composition can be administered shortly before, at or about the same time, or shortly after another composition.

One, two, three, or more, or all of the steps of generating a synthetic neoepitope peptide, generating a synthetic antibody, contacting a bodily fluid, and detecting the bound synthetic antibody may be performed prior to treatment of the patient with immune therapy. Once a patient has begun treatment, a bodily fluid may be obtained and a synthetic antibody specific to the neoepitope may be used to detect the presence of a cellular component comprising the neoepitope. If the level of neoepitope remains about the same or has increased in the bodily fluid, as compared to the level prior to treatment, it may be concluded that the treatment is not working and a different therapeutic treatment may need to be selected.

At least one, two, three, or more, or all of the steps of generating a synthetic neoepitope peptide, generating a synthetic antibody, contacting a bodily fluid, and detecting the bound synthetic antibody may be performed after at least a first round of treatment of the patient with immune therapy. Once a patient has begun treatment, a bodily fluid may be obtained and a synthetic antibody specific to the neoepitope may be used to detect the presence of a cellular component comprising the neoepitope. If the level of neoepitope remains about the same or has increased in the bodily fluid, as compared to the level prior to treatment, it may be concluded that the treatment is not working and a different therapeutic treatment may need to be selected.

In some embodiments, multiple neoepitopes of the same cancer may be targeted. In this regard, an antibody may be generated against each neoepitope and the combination of antibodies may be administered to the patient as combination therapy.

In other embodiments, a tumor mass may be heterogeneous with different tumor cells of the same mass expressing different antigens and therefore different neoepitopes. In this regard, more than one neoepitope may be selected as a therapeutic target. For example, an antibody may be generated against each neoepitope and the combination of antibodies may be administered to the patient as combination therapy.

In still other embodiments, a neoepitope that is present in two or more subclones of the tumor of the patient is selected as a therapeutic target. In some cases, tumors may be heterogeneous and may have different subclones with different mutations and therefore different neoepitopes being displayed. In such cases, each subclone may be subject to omics analysis to identify common neoepitopes between the subclones.

Example 1. Obtaining a Tumor from a Patient

In some embodiments, a biopsy of a tumor from a patient is obtained, e.g., using fine needle aspiration. The biopsy is propagated in cell culture and aliquoted into multiple samples. At least one sample is prepared for omics analysis using standard techniques in the art. Another sample is frozen according to standard protocols and stored for additional omics analysis, as needed. If possible, a sample of a matched normal control and/or a blood sample to determine HLA type is also obtained from the patient at the time the biopsy of the tumor is performed.

Example 2. Sequencing a Tumor from a Patient and Identifying Neoepitopes in Silico Cells from the tumor biopsy are propagated/maintained using standard techniques of mammalian cell culture. The cells may be prepared for omics analysis, e.g., DNA sequencing, RNA expression and quantification, mass spectrometry analysis, immunocytochemistry analysis, etc., according to techniques known the in art.

Similarly, cells from the matched control are propagated/maintained using standard techniques of mammalian cell culture. The cells may be prepared for omics analysis, e.g., DNA sequencing, RNA expression and quantification, mass spectrometry analysis, immunocytochemistry analysis, etc., according to techniques known the in art. If a matched control is not available, a normal sample (e.g., from a different tissue) may be substituted, or alternatively, a profile stored in a database (e.g., an aggregate of normal samples from different individuals) can be used.

In some embodiments, DNA is extracted from the cells, purified according to standard techniques known in the art and provided to a high throughput sequencer for whole genome sequencing, exome sequencing or sequencing of other specified regions.

The tumor cells and the matched normal control cells are sequenced separately according to techniques known in the art, and the resultant sequences are aligned using bioinformatics alignment tools as referenced herein (e.g., BAM-BAM as described in WO 2013/074058 or WO 2011/149534). Based on this comparison, the number and location of mutations of the tumor cell can be ascertained. RNA expression and quantification (e.g., RNA-Seq) may also be performed separately on tumor cells and the matched normal control cells.

In some embodiments, a patient's HLA haplotype is also determined, e.g., from a blood sample from the patient or using in silico methods as described herein, according to standard protocols known in the art (see e.g., WO 2017/035392).

Neoepitope sequence data comprising the tumor mutations (pool of candidate mutations) are analyzed by a MHC epitope prediction program, e.g., such as NetMHC. The MHC epitope prediction program identifies neoepitopes in silico that are predicted to bind to a MHC class I receptor. In instances in which a patient's HLA haplotype is available, the MHC epitope prediction program can also be configured to perform docking simulations between the candidate neoepitope and a MHC class I molecule that is the same or similar to the patient.

In further embodiments, the pool of candidate neoepitopes may be refined based on other characteristics, including predicted ability to be transported through the TAP inhibitor, resistance to intracellular degradation, ability to be transported through the Golgi apparatus, and any other factors which would influence successful presentation of the neoepitope on the surface of the cell.

In further embodiments, the pool of candidate neoepitopes may be refined based on other characteristics, including whether the neoantigen is likely to be displayed on the surface of the cell (e.g., whether a transmembrane domain is present in the neoantigen as well as whether the neoepitope is solvent exposed and not buried).

Candidate neoepitopes may be further refined based on expression levels, if RNA profiling is performed in addition to DNA sequencing. For a neoepitope to be expressed on the surface of a cell, it should be expressed at a high enough frequency to be visible to the cell and therefore be processed, e.g., according to the MHC class I pathway. Thus, in some embodiments, candidate neoepitopes that are expressed at low frequencies can be excluded, as these neoepitopes would not be expected to be visible to the MHC class I pathway.

Thus, from this combined analysis, one or more neoepitopes may be identified in silico for synthesis.

Example 3. Generating a Synthetic Neoepitope Peptide

Once a candidate neoepitope has been identified in silico, it may be synthesized according to known techniques in the art, e.g., solid phase peptide synthesis (see, e.g., https://www.chem.uci.edu/~jsnowick/groupweb/files/Standard_practices_for_Fmoc_based_solid_phase_peptide_synthesis_in_the_Nowick_Laboratory_V_1point6.pdf).

Once generated, the synthetic peptide can be utilized as part of a phage display or mRNA display screen in order to identify synthetic antibodies (e.g., antibody fragments such as scFvs) capable of binding to the synthetic neoepitope peptide.

Example 4. Generating a Synthetic Antibody Against the Synthetic Neoepitope Peptide In phage display methods, functional antibody domains are displayed on the surface of phage particles, which carry the polynucleotide sequences encoding them. In particular, DNA sequences encoding VH and VL domains are amplified from cDNA libraries (e.g., human or murine cDNA libraries of lymphoid tissues) or synthetic cDNA libraries. The DNA encoding the VH and VL domains are joined together by a scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the pIII, pVIII, pVI, or pIX phage gene, or based on T7 phages and the gene 10 capsid protein. Phage expressing an antigen binding domain that binds to an antigen of interest (i.e. the synthetic neoepitope peptide) can be selected or identified with antigen, e.g., using labeled antigen or antigen bound or captured to a solid surface or bead. Examples of phage display methods that can be used to make the antibodies described herein are well known in the art (see, Osbourn et al., *Nat. Biotechnol.* (1998) 16:778-81).

Alternatively, in mRNA display methods, a scFv library is generated and transcribed in vitro, and the mRNA transcript is ligated to puromycin. The mRNA is then translated in vitro and the resultant antibody fragment (e.g., a scFV) is covalently linked to its encoding mRNA through puromycin. In some embodiments, the synthetic neoepitope peptide is ligated to a bead or other surface. The mRNA/antibody fragment complexes are brought into contact with the synthetic peptide under conditions suitable to promote binding, and non-binders are washed away. The bound molecules may be eluted by protease digestion or other suitable means of obtaining the mRNA. The mRNA is then reverse transcribed into cDNA for cloning, amplification and sequencing (see, Fukuda, *Nucleic Acids Res.* (2006) 34(19): 1-8). mRNA display for selection of antibodies from large repertoires is also described in, e.g., Brekke & Sandlie, *Nat. Rev. Drug Discovery* (2003) 2:52-62 and U.S. Pat. No. 8,623,358.

Based on these techniques, antibodies or fragments thereof that bind to a given synthetic neoepitope peptide can be identified and isolated for subsequent use.

Example 5. Detection of the Neoepitope on the Tumor Cell Using a Synthetic Antibody Once synthetic antibodies having specificity for the synthetic neoepitope peptides have been isolated, these synthetic antibodies can be used to test for display of the neoepitope on the tumor cells.

The antibody can be labeled with any detectable means known in the art for detecting binding of synthetic antibodies to neoepitopes displayed on the surface of the cells. A variety of techniques are suitable for detecting binding of an antibody to a cellular component (https://www.rndsystems.com/resources/protocols/detection-visualization-antibody-binding). The synthetic antibody may be labeled with a colorimetric probe, a fluorescent tag, a chemiluminescent tag, or a radiolabel, and incubated with the bodily fluid comprising cells or cellular components.

For example, live cells may be plated on a glass or plastic surface. Alternatively, other surfaces may be coated with materials to promote binding, e.g., poly-lysine coatings, gelatin, collagen, fibronectin, laminin, etc. After incubation of the tumorigenic cells with the detectable synthetic antibody, excess unbound synthetic antibody can be removed using a wash step. The remaining cells, adhered to the surface, can undergo imaging or other colorimetric analysis to determine whether the synthetic antibody is present. A similar protocol can be applied to membrane fragments, by fixing such fragments to a surface prior to incubation with the detectable synthetic antibody.

Such techniques, including various fluorescently tagged, colorimetric, chemiluminescent, or radiolabeling immunoassays, are well known to a skilled artisan.

If the identified neoepitope is present on the surface of the tumor cell, binding between the antibody and the neoepitope will be detected. If antibody binding is not detected, then it may be concluded that the neoepitope is not present on the surface of the cell, and a different in silico identified neoepitope will need to be selected as a therapeutic target.

Example 6. Isolation of Tumor Cells

Various protocols exist for isolating cells using antibodies. In some embodiments, cells may be isolated using commercially available kits (e.g., Thermo Scientific, at https://tools.thermofisher.com/content/sfs/manuals/dynabeads_flowcompflexi_buffywb_man.pdf), e.g., from ThermoScientific (e.g., Dynabeads Flow Comp Flexi Kit). For example, the synthetic antibodies specific to the neoepitope may be labeled with DBS-X biotin, and incubated with tumorigenic cells expressing the neoepitope. Beads (e.g., Dynabeads), may be added to bind to the DBS-X biotin labeled antibodies, and an external magnet may be applied to separate bound cells from non-bound cells. After isolation, the beads are released by altering buffer conditions, and the magnet is used to isolate the beads from the cells. The isolated cells can be used in any downstream process.

In other embodiments, the synthetic antibodies are coupled to a surface. When these antibodies bind to the neoepitope displayed on the surface of a tumor cell, e.g., a CTC cell, the cell population expressing the neoepitope can be enriched, and other cells and contaminants can be washed away. In this case, it is generally understood that the surface is non-adherent, and that tumor cells are not adherent to the surface unless displaying ligand for the synthetic antibody.

In still other embodiments, antibodies are coupled to a fluorescent dye, allowing specific cells expressing the neoepitope to be labeled. The labeled cells can then be separated using a fluorescence activated cell sorter (FACs) (see, for an example protocol, http://www.abcam.com/protocols/fluorescence-activated-cell-sorting-of-live-cells).

In still other embodiments, microfluidic devices may be used to enrich tumor cells displaying neoepitopes. In many cases, tumor cells are larger than blood cells, e.g., tumor cells may range in size from 10-20 µm in diameter while blood cells may range from 7-12 µm in diameter. Microchips can be designed to separate cells based on size, allowing for enrichment of tumor cells (Warkiani et al., Lab Chip, (2014) 14:128-137; Ozkumur et al., Sci Transl Med (2013) 5:179ra47).

Example 7. Detection of an Immune Response

Once the presence of the neoepitope has been validated, the ability of the synthetic antibody to elicit an immune response may be tested. A variety of assays for monitoring cellular immune responses in vivo and in vitro are available (see, Clay T. et al., Clin. Cancer Res. (2001) &:1127-1135).

In some embodiments, a blood sample may be drawn from a patient and tumor cells isolated. T cells, which may also be derived from the patient, may be incubated with the tumor cells and a synthetic antibody specific for the neoepitope. The solution can be monitored to determine whether an immune response is triggered, e.g., by detecting a release of cytotoxic granules, phagocytosis, or receptor-ligand mediated cytolysis.

Traditional assays for measuring cell lysis include addition of a radioisotope, e.g., $^{51}Cr$, to cell culture, which is trapped in the interior of living cells. The radioisotope is released upon cell lysis into the extracellular fluid, providing an indicator of the amount of lysis occurring.

Other assays exist in which levels of Granzyme B are measured. Granzyme B is secreted by activated cytotoxic T cells or NK cells. Granzyme B is released through exocytosis, and in conjunction with perforin, is able to enter target cells to help trigger cell death. Enzyme linked immunoassays (e.g., ELISpot, an ELISA sandwich assay) are known in the art for quantifying the amount of secreted Granzyme B. Essentially, cells are incubated in the presence of antibodies specific for Granzyme B. The cells are removed, and a second Granzyme B specific antibody is added with a detectable marker (e.g., biotin/alkaline phosphatase streptavidin complex). Based on the intensity of color formation, the amount of Granzyme B can be quantified (see, https://www.rndsystems.com/products/human-granzyme-b-elispot-kit_e12906#product-details; Malyguine A. et al., Cells (2012) 1(2): 111-126).

In other embodiments, cytotoxic T cells can be engineered to express a chimeric antigen receptor, wherein specificity for the neoepitope has been grafted to the CAR receptor based on the synthetic antibody. The CAR T-cells can be brought into contact with the tumorigenic cells, and an immune response can be monitored according to techniques presented herein.

Example 8. Detection of an Effect of a Chemotherapeutic Drug

Similarly, once the presence of the neoepitope has been validated, a chemotherapeutic drug may be incubated with the tumor cells. A variety of assays for monitoring chemotherapeutic responses are available (see, Hoffman R., J. Clin. Lab Analysis (1991) 5:133-143).

In some embodiments, tumor tissue is obtained from the patient and is subjected to mammalian tissue culture (e.g., 10% fetal calf serum, 2 mM glutamine, antibiotic at standard concentration) at 37 C, 95% oxygen, 5% $CO_2$ for 1 to 5 days. Once the cells are adjusted to cell culture, the chemotherapeutic is added, using calculated maximal plasma concentrations (e.g., 5-fluorouracile (5-FU), 20 µg/ml; methotrexate (MTX), 12 µg/ml; cyclophosphamide (CPA), 30 µg/ml; vinblastine (VBL), 0.2 µg/ml; doxorubicine (DOX), 0.9 µg/ml; taxole (TXL), 2.4 µg/ml; or vincristine, 0.03 µg/ml, etc.). The cells are then assayed (and are compared to an untreated control) to determine the response, e.g., changes in morphology, the number of surviving cells, etc.).

Example 9. Example Flow Chart

As an example, a flow chart describing a method of making and using a synthetic antibody as described herein is presented in FIG. 1. At step 110, a sample of a patient tumor is obtained. At step 120, omics analysis is performed on the tumor cells. At step 130, a neoepitope predicted to bind to a MHC is identified based on in silico techniques. Additional filtering may occur. At step 140, a synthetic neoepitope peptide is generated based on the identified neoepitope. At step 150, a synthetic antibody is generated to the synthetic neoepitope peptide. At step 160, a bodily fluid sample is obtained from the patient. At step 170, the bodily fluid is contacted with the synthetic antibody. At step 180, the bound antibody to the neoepitope on the surface of the cell (obtained from the bodily fluid) is detected. Of course, it is understood that if the neoepitope is not present or not exposed on the tumor cell surface, detection will not occur.

Example 10. Example Flow Chart

Figure 2:
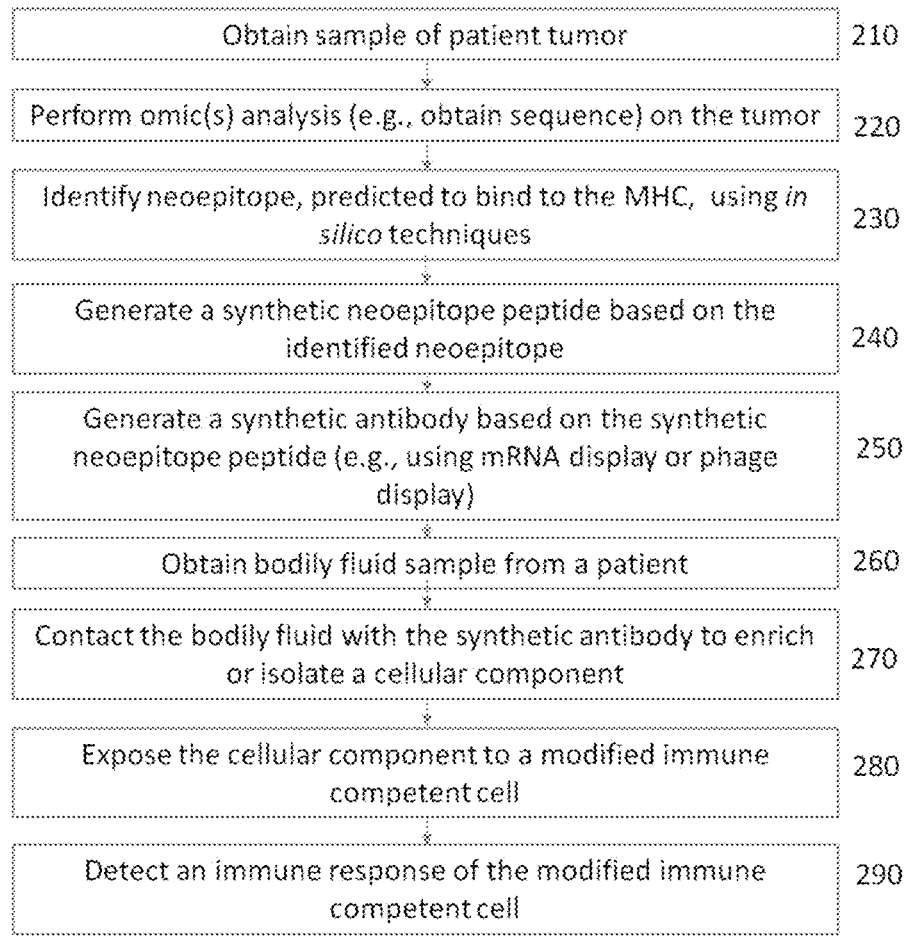
FIG. 2 shows a flow chart describing an exemplary embodiment of the techniques presented herein.

As another example, a flow chart describing making and using an antibody as described herein is presented in FIG. 2. At step 210, a sample of a patient tumor is obtained. At step 220, omics analysis is performed on the tumor cells. At step 230, a neoepitope predicted to bind to a MHC is identified based on in silico techniques. Additional filtering may occur. At step 240, a synthetic neoepitope peptide is generated based on the sequence of the identified neoepitope. At step 250, a synthetic antibody is generated to the synthetic neoepitope peptide. At step 260, a bodily fluid sample is obtained from the patient. At step 270, the bodily fluid is contacted with the synthetic antibody to enrich or isolate a cellular component. At step 280, the cellular component is incubated with a modified immune component cell (e.g., such as an engineered NK cell, a CAR T cell, a dendritic cell engineered to express a co-stimulatory signal, etc.), and at step 290, an immune response of the modified immune competent cell is detected. Of course, it is understood that if the neoepitope is not present or exposed on the tumor cell surface, enrichment of the cells will not occur.

Example 11. Example Flow Chart

Figure 3:
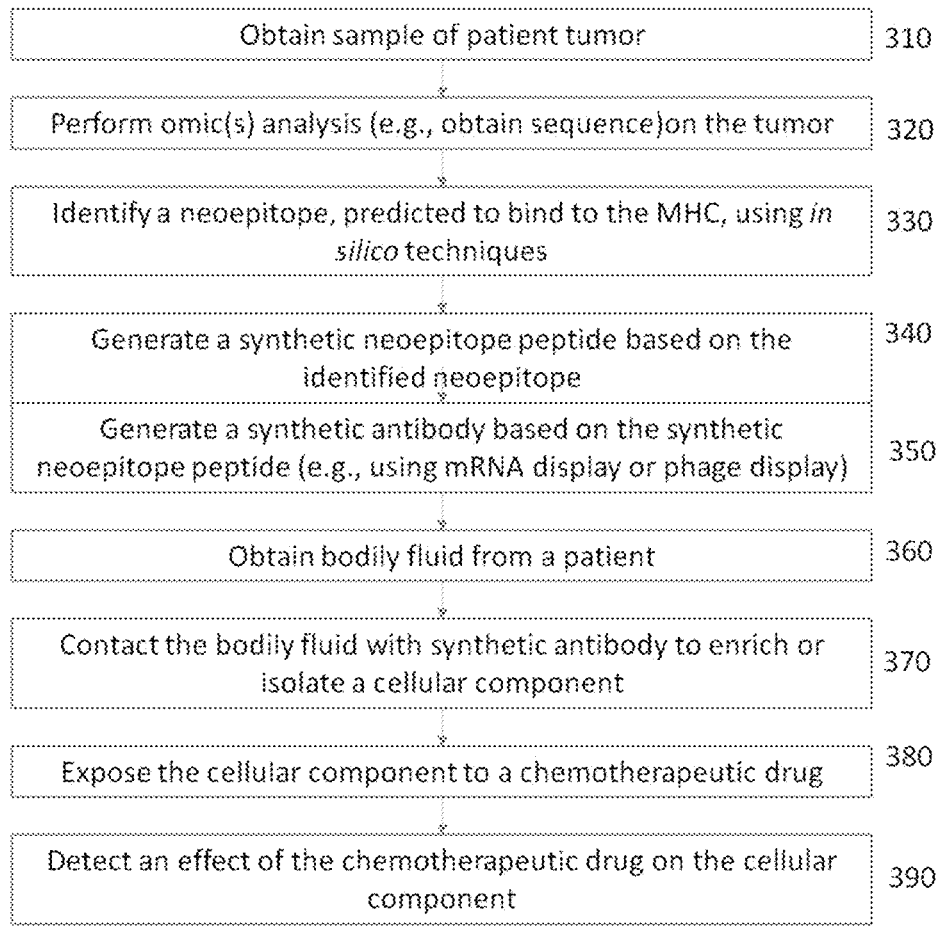
FIG. 3 shows a flow chart describing an exemplary embodiment of the techniques presented herein.

As another example, a flow chart describing making and using an antibody as described herein is presented in FIG. 3. At step 310, a sample of a patient tumor is obtained. At step 320, omics analysis is performed on the tumor cells. At step 330, a neoepitope predicted to bind to the MHC molecule is identified based on in silico techniques. Additional filtering may occur. At step 340, a synthetic neoepitope peptide is generated based on the sequence of the identified neoepitope. At step 350, a synthetic antibody is generated based on the synthetic neoepitope peptide. At step 360, a bodily fluid is obtained from the patient. At step 370, the bodily fluid is contacted with the synthetic antibody to enrich or isolate a cellular component. At step 380, the cellular component is incubated with a chemotherapeutic drug, and at step 390, an effect of the chemotherapeutic drug is detected. Of course, it is understood that if the neoepitope is not present or exposed on the tumor cell surface, enrichment of the cells will not occur.

These examples are purely intended to be exemplary and are not intended to be limiting, as numerous different embodiments are understood to fall within the scope of the present disclosure.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An in-vitro method of validating an immune therapy that targets a neoepitope of a tumor of a patient, comprising:
    generating, in-vitro, a synthetic antibody that binds to the neoepitope;
    contacting, in-vitro, a bodily fluid of the patient with the synthetic antibody under conditions to allow binding of the synthetic antibody to a cellular component in the bodily fluid to thereby enrich or isolate the cellular component, wherein the cellular component is a cell or membranous material and displays the neoepitope on its surface;
    exposing the cellular component to an immune competent cell that has been modified so as to express a chimeric antigen receptor or a chimeric co-stimulatory molecule with an intracellular signaling domain, and further exposing the cellular component to a chemotherapeutic agent; and
    detecting an immune response of the immune competent cell and detecting the effect of the chemotherapeutic drug on the cellular component.

2. The method of claim 1, wherein the neoepitope is patient- and tumor-specific.

3. The method of claim 1, wherein the neoepitope is bound to at least one of (a) a major histocompatibility class I (MHC class I) molecule and (b) a major histocompatibility class II (MHC class II) molecule of the patient.

4. The method of claim 1, wherein the neoepitope is a tumor associated antigen or a cancer specific antigen.

5. The method of claim 1, wherein the neoepitope further comprises one or more additional amino acids attached either to the N-terminus or the C-terminus of the neoepitope, wherein the additional amino acids function to increase binding of the synthetic neoepitope peptide to the cellular component or to bind to a second neoepitope on the cellular component.

6. The method of claim 1, wherein the synthetic antibody is generated by mRNA display or phage display.

7. The method of claim 1, wherein the synthetic antibody is a scFv, a scFv-Fc, an Fv, a Fab, a Fab', a $F(ab')_2$, an Fd, an IgG, an IgM, or an active fragment thereof.

8. The method of claim 7, wherein complementarity determining regions (CDRs) of the synthetic antibody are grafted onto a human or humanized antibody backbone or scaffold.

9. The method of claim 1, wherein the bodily fluid is whole blood or a fraction thereof, lymphatic fluid, urine, interstitial fluid, or saliva.

10. The method of claim 1, wherein contacting is performed in a microfluidic device or in fluorescence-activated cell sorting (FACS).

11. The method of claim 1, wherein the cellular component is a circulating tumor cell, a metastatic cell, a circulating microvesicle, a circulating exosome, or a circulating membrane fragment.

12. The method of claim 1, wherein detecting comprises optical detection, radiometric detection, or quantitative detection to determine a level of a neoepitope on the cellular component, and when the level of the neoepitope has not decreased subsequent to treatment to eliminate or reduce the tumor, modifying the treatment that is administered to the patient.

13. The method of claim 1, wherein detecting comprises isolating the cellular component using the bound synthetic antibody.

* * * * *